(12) United States Patent
Park et al.

(10) Patent No.: US 11,957,709 B2
(45) Date of Patent: *Apr. 16, 2024

(54) OXYGEN GAS SUSTAINED RELEASED NANO-EMULSION COMPOSITION AND METHOD FOR PRODUCING THE SAME

(71) Applicants: AMOREPACIFIC CORPORATION, Seoul (KR); CHOSUN NATIONAL UNIVERSITY INDUSTRY-ACADEMIC COOPERATION FOUNDATION, Gwangju (KR)

(72) Inventors: Phil June Park, Yongin-si (KR); Jun-pil Jee, Gwangju (KR); Bongsoo Pi, Yongin-si (KR); Haewon Jeong, Yongin-si (KR); Hyoung June Kim, Yongin-si (KR); Dalsu Na, Yongin-si (KR); Wonseok Park, Yongin-si (KR)

(73) Assignees: AMOREPACIFIC CORPORATION, Seoul (KR); CHOSUN NATIONAL UNIVERSITY INDUSTRY-ACADEMIC COOPERATION FOUNDATION, Gwangju (KR)

(*) Notice: Subject to any disclaimer, the term of this patent is extended or adjusted under 35 U.S.C. 154(b) by 0 days.

This patent is subject to a terminal disclaimer.

(21) Appl. No.: 17/847,808

(22) Filed: Jun. 23, 2022

(65) Prior Publication Data
US 2023/0000902 A1 Jan. 5, 2023

(30) Foreign Application Priority Data

Jun. 24, 2021 (KR) .................. 10-2021-0082583
Dec. 15, 2021 (KR) .................. 10-2021-0179674

(51) Int. Cl.
*A61K 33/00* (2006.01)
*A61K 9/00* (2006.01)
(Continued)

(52) U.S. Cl.
CPC ............ *A61K 33/00* (2013.01); *A61K 9/0014* (2013.01); *A61K 9/0019* (2013.01);
(Continued)

(58) Field of Classification Search
CPC .................................................... A61K 33/00
See application file for complete search history.

(56) References Cited

U.S. PATENT DOCUMENTS

2004/0057906 A1* 3/2004 Hsu ................. C09K 23/017
424/45
2010/0144861 A1* 6/2010 Huvard ................ A61P 17/00
514/747
(Continued)

FOREIGN PATENT DOCUMENTS

DE 10 2004 001 267 A1 8/2005
DE 102004001267 A1 * 8/2005 ............... A61K 8/21
(Continued)

OTHER PUBLICATIONS

Huamin Hu, Xuefeng Yan, Hui Wang, Joji Tanaka, Mengzhe Wang, Wei You and Zibo Li. "Perfluorocarbon-based O2 nanocarrier for efficient photodynamic therapy." Journal of Materials Chemistry B, VI. 7, 2019, pp. 1116-1123. (Year: 2019).*
(Continued)

Primary Examiner — Isaac Shomer
(74) Attorney, Agent, or Firm — Sughrue Mion, PLLC

(57) ABSTRACT

The present disclosure relates to a nanoemulsion composition of oxygen gas sustained release and method for preparing the same, and provides a nanoemulsion composition of oxygen gas sustained release and method for preparing
(Continued)

the same, including a water phase part containing water, and an oil phase part dispersed in the water phase part and made of nanoparticle containing a perfluorocarbon compound, wherein the oil phase part contains oxygen gas, and the oxygen gas is released in sustained release. According to the present disclosure, there are advantages of preventing hair loss or promoting hair growth by increasing the amount of oxygen gas supplied to the hair bulb and the oxygen release time from the hair bulb.

17 Claims, 24 Drawing Sheets

(51) Int. Cl.
      *A61K 9/06*       (2006.01)
      *A61K 9/107*       (2006.01)
      *A61K 9/16*       (2006.01)
      *A61K 9/48*       (2006.01)
      *A61K 47/02*       (2006.01)
      *A61K 47/10*       (2017.01)
      *A61K 47/12*       (2006.01)
      *A61K 47/20*       (2006.01)
      *A61K 47/24*       (2006.01)
      *A61K 47/26*       (2006.01)
      *A61K 47/36*       (2006.01)
      *A61K 47/38*       (2006.01)
      *A61K 47/44*       (2017.01)
      *A61P 17/14*       (2006.01)
(52) U.S. Cl.
      CPC .............. *A61K 9/0095* (2013.01); *A61K 9/06* (2013.01); *A61K 9/1075* (2013.01); *A61K 9/1617* (2013.01); *A61K 9/4858* (2013.01); *A61K 47/02* (2013.01); *A61K 47/10* (2013.01); *A61K 47/12* (2013.01); *A61K 47/20* (2013.01); *A61K 47/24* (2013.01); *A61K 47/26* (2013.01); *A61K 47/36* (2013.01); *A61K 47/38* (2013.01); *A61K 47/44* (2013.01); *A61P 17/14* (2018.01)

(56) References Cited

U.S. PATENT DOCUMENTS

| | | | |
|---|---|---|---|
| 2011/0306581 A1* | 12/2011 | Rapoport | A61K 31/56 435/375 |
| 2013/0324567 A1 | 12/2013 | Liu | |
| 2016/0166716 A1 | 6/2016 | Irudayaraj et al. | |
| 2023/0000902 A1* | 1/2023 | Park | A61K 33/00 |

FOREIGN PATENT DOCUMENTS

| | | |
|---|---|---|
| KR | 10-2010-0116882 A | 11/2010 |
| WO | 2010/121082 A2 | 10/2010 |
| WO | 2012/040342 A2 | 3/2012 |
| WO | 2016/108233 A1 | 7/2016 |

OTHER PUBLICATIONS

Nagamune Nishikido, Walter Mahler, and Pasupati Mukerjee. "Interfacial Tensions of Perfluorohexane and Perfluorodecalin against Water." Langmuir, vol. 5, No. 1, 1989, pp. 227-229. (Year: 1989).*
ICI Americas Inc. "The HLB SYSTEM a Time-Saving Guide to Emulsifier Selection." ICI Americas Inc., Wilmington, Delaware, Revised Mar. 1980, pp. 1-22. (Year: 1980).*
Gozlan et al. "Preparation of amphiphilic sorbitan monoethers through hydrogenolysis of sorbitan acetals and evaluation as bio-based surfactants." Green Chemistry, vol. 18, 2016, pp. 1994-2004. (Year: 2016).*
F. Corrales Chahar, S.B. Díaz, A. Ben Altabef,, C. Gervasi, P.E. Alvarez. "Characterization of interactions of eggPC lipid structures with different biomolecules." Chemistry and Physics of Lipids, vol. 210, 2018, pp. 60-69. (Year: 2018).*
Alexandra M. Walsh et al. "A Surfactant Copolymer Facilitates Functional Recovery of Heat-Denatured Lysozyme." Annals of the New York Academy of Sciences, vol. 1066, 2005, pp. 321-327. (Year: 2005).*
Usman Taqui Syed et al. "Studies on the formation and stability of perfluorodecalin nanoemulsions by ultrasound emulsification using novel surfactant systems." Colloids and Surfaces A: Physicochemical and Engineering Aspects, vol. 616, 2021, 126315, pp. 1-12 and 6 pages of supplementary information. (Year: 2021).*
Google Patents. English Translation of DE102004001267A1. Obtained from https://patents.google.com/patent/DE102004001267A1/en?oq=emulsion+perfluorocarbon+oxygen+hair on Jan. 31, 2023, originally published 2005, pp. 1-18. (Year: 2005).*
Jun-Pil Jee, et al., "Preparation and in vivo evaluation of a topical hydrogel system incorporating highly skin-permeable growth factors, quercetin, and oxygen carriers for enhanced diabetic wound-healing therapy", International Journal of Nanomedicine, 2019, pp. 5449-5475, vol. 14.
Flores Aimee, et al., "Lactate dehydrogenase activity drives hair follicle stem cell activation", Nature Cell Biology, 2017, pp. 1017-1026, vol. 19, No. 9.
Kenneth C. Lowe, "Perfluorochemical respiratory gas carriers: applications in medicine and biotechnology", Science Progress, 1997, pp. 169-193, vol. 80, No. 2.
Extended European Search Report dated Dec. 6, 2022 in Application No. 22180288.7.
Johannes Jägers et al., "Perfluorocarbon-based oxygen carriers: from physics to physiology", Pflügers Archiv—European Journal of Physiology, 2020, vol. 473, No. 2, pp. 139-150 (12 pages total).

* cited by examiner

OXYGEN GAS SUSTAINED RELEASED NANO-EMULSION COMPOSITION AND METHOD FOR PRODUCING THE SAME

CROSS REFERENCE TO RELATED APPLICATION

The present application claims priority to Korean Patent Applications Nos. 10-2021-0082583, filed Jun. 24, 2021, and 10-2021-0179674, filed Dec. 15, 2021, the entire contents of which is incorporated herein for all purposes by this reference.

BACKGROUND OF THE INVENTION

Field of the Invention

The present specification discloses a nanoemulsion composition of oxygen gas sustained release and method for preparing the same, including a water phase part containing water; and an oil phase part dispersed in the water phase part and made of nanoparticle containing a perfluorocarbon compound, wherein the oil phase part contains oxygen gas and the oxygen gas is released in sustained release.

Description of the Related Art

Most animals shed and regrow hair seasonally, but humans shed about 100 strands of hair out of about 100,000 strands and about 100 strands regrow every day, thus always maintaining a similar number. Although hair is not an organ critical in sustaining life, it is an indicator of health state and an important part of the body in terms of appearance. Whereas hair loss is considered a normal physiological event for those with a lot of hair, those who suffer from severe hair loss can be badly affected in terms of mental well-being and quality of life due to depression, sense of shame, social isolation, etc.

The hair growth cycle consists of anagen, catagen and telogen phases. During the anagen phase, hair growth is promoted as cell division occurs actively in the hair dermal papilla, and hair grows only in this stage. Considering that the anagen is about 3 to 5 years for men and about 4 to 6 years for women, about 80 to 85% of hair is in the anagen phase. In the catagen phase, which lasts about 3 to 4 weeks, the cell division declines gradually. Lastly, in the telogen phase, the hair dermal papilla is withdrawn and the hair separated from the capillary vessel and simply stuck in the scalp. This lasts about 3 months and the hair in the telogen phase is easily lost upon physical stimulation.

Korean Patent Laid-Open Publication No. 10-2010-0116882 discloses that a composition containing a natural extract can be applied to prevent hair loss or promote hair growth. However, according to the process (hair loss) of the scalp becoming bald, the microvessels connected to the hair roots are thinned, which results in insufficient oxygen supply through the microvessels. As the basis for hair loss scalp due to insufficient oxygen, there has been a report that lactate, which occurs when oxygen metabolism is insufficient, is accumulated. There has been a report that the activity of hair stem cells is increased again when an enzyme (lactate dehydrogenase) that degrades the lactate is treated. To summarize, oxygen is the most important element in promoting or maintaining the growth of dermal papilla cells, which are located in the center of the hair follicle and are the basis of new hair generation (Non-Patent Document 1).

Oxygen for activating the metabolism of dermal papilla cells is a gas, so it cannot penetrate the skin in a general way. Accordingly, there is a need for research and development on a composition capable of preventing hair loss or promoting hair growth by increasing the amount of oxygen supplied to the hair bulb.

SUMMARY OF THE INVENTION

The present disclosure has been devised to solve the above problems, and an object of the present disclosure is to provide a composition and method for preparing the same capable of preventing hair loss or promoting hair growth by increasing the amount of oxygen gas supplied to the hair bulb and the oxygen release time from the hair bulb.

In order to achieve the object of the present disclosure described above, the present disclosure provides a nanoemulsion composition of oxygen gas sustained release and method for preparing the same, including a water phase part containing water, and an oil phase part dispersed in the water phase part and made of nanoparticle containing a perfluorocarbon compound, wherein the oil phase part contains oxygen gas, and the oxygen gas is released in sustained release.

According to the present disclosure, there is an advantage of preventing hair loss or promoting hair growth by increasing the amount of oxygen gas supplied to the hair bulb and the oxygen release time from the hair bulb.

DETAILED DESCRIPTION

Figure 1:
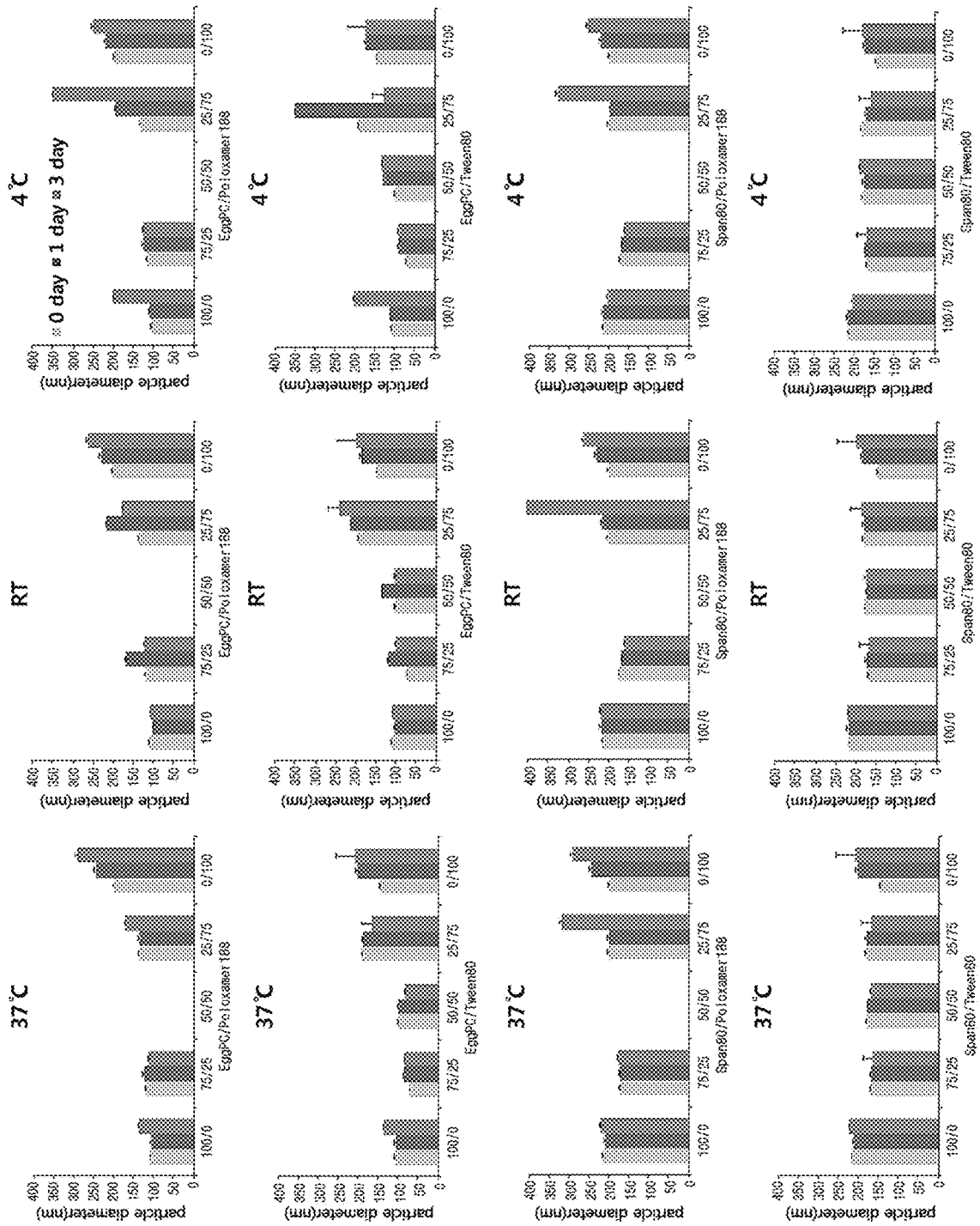
FIG. 1 is a graph showing a size of nanoemulsion according to the type and content ratio of a surfactant and an auxiliary surfactant.

The terms used in this specification have been selected as currently widely used general terms as possible while considering the functions in the present disclosure, which may vary depending on the intention, precedent, or emergence of new technology of those skilled in the art. In addition, in a specific case, there is a term arbitrarily selected by the applicant, and in this case, the meaning will be described in detail in the description of the corresponding invention. Therefore, the terms used in the present disclosure should be defined based on the meaning of the term and the contents of the present disclosure, rather than the simple name of the term.

Unless defined otherwise, all terms used herein, including technical and scientific terms, have the same meaning as commonly understood by those skill in the art to which this invention belongs. Generally understood terms should be interpreted as having the same meaning as they have in the context of the related art, and are not to be interpreted in an ideal or excessively formal meaning unless explicitly defined in the present disclosure.

Numerical ranges are inclusive of the numerical values defined in this disclosure. Every maximum numerical limitation given throughout this specification includes all lower numerical limitations as if the lower numerical limitation were expressly written. Every minimum numerical limitation given throughout this specification includes all higher numerical limitations as if the higher numerical limitation were expressly written. Any numerical limitation given throughout this specification shall include all numerical ranges within the broader numerical range, as if the narrower numerical limitation were expressly written.

As used herein, the words "comprising," "having," "containing," are inclusive or open-ended and do not exclude additional unrecited elements or method steps. As used herein, the term "or combinations thereof" refers to all permutations and combinations of items listed prior to the term. For example, "A, B, C, or a combination thereof" means A, B, C, AB, AC, BC or ABC, and it is intended to include at least one of BA, CA, CB, CBA, BCA, ACB, BAC or CAB where order is important in a particular context. With this example, combinations containing repetitions of one or more items or terms are expressly included, such as BB, AAA, MB, BBC, AAABCCCC, CBBAAA, CABABB, and the like. One of ordinary skill in the art will understand that there is typically no limit to the number of items or terms in any combination, unless the context makes it clear otherwise.

Hereinafter, the present disclosure will be described in detail with reference to examples and drawings. However, it is obvious that the present invention is not limited by the following examples and drawings.

In one aspect, the present disclosure provides a nanoemulsion composition of oxygen gas sustained release including a water phase part containing water; and an oil phase part dispersed in the water phase part and made of nanoparticle containing a perfluorocarbon compound, wherein the oil phase part contains oxygen gas, and the oxygen gas is released in sustained release.

Unlike microemulsion, nanoemulsion is a kinetically stable emulsion, and since there is no aggregation or coalescence between particles, it is stable for a long period of time even under low viscosity conditions. The reason why the nanoemulsion is used as a useful formulation is that (1) the particles are very small, so they are not affected by gravity due to the Brownian motion of the particles, so they are free from precipitation or creaming, (2) that there is no aggregation phenomenon with small particles, so the possibility of emulsion separation is low, (3) that small particles can prevent coalescence due to less deformation of the particles, (4) that it can improve skin penetration of active ingredients by retaining a wide interfacial membrane with small particles, and (5) that it can be prepared with significantly less amount of surfactant compared to microemulsions. The nanoemulsion may be an oil-in-water (O/W) emulsion.

The "oxygen gas" may be naturally occurring oxygen or synthetically produced oxygen. In general, it is known that the oxygen concentration in the atmosphere is at a level of 20 to 22%, and an oxygen condition of about 20% is called a normoxia condition. An oxygen condition of 1 to 5% is called a hypoxia condition, and an oxygen condition of 1% or less is called an extreme hypoxia (or anoxia) condition. Since hair follicles can grow in an oxygen condition of 0.1 to 0.8%, it is necessary to maintain the oxygen condition in order to prevent hair loss or promote hair growth.

In the present disclosure, the term "immediate release" refers to a drug in which active ingredients are released immediately, and is a formulation that releases most of the active ingredients within a few seconds. In contrast, the term "sustained release" refers to a formulation that releases active ingredients slowly for several tens of seconds to several hours, and is designed to maintain an effective amount of the active ingredients over a relatively long period of time. It refers to a formulation with fewer side effects because the number of administrations is less than that of a general drug and the bioreaction is uniform because of the characteristic of a "sustained release" formulation that lasts for a certain period of time after reaching a therapeutic blood concentration. The nanoemulsion composition of the present disclosure exhibits a "oxygen gas sustained release" profile, thereby releasing oxygen for a period of at least 10 seconds or maintaining an oxygen condition favorable for preventing hair loss or promoting hair growth.

According to one embodiment of the present disclosure, the average diameter of the nanoparticles may be 100 nm to 300 nm. More specifically, the average diameter of the nanoparticles may be 100 nm or more, 110 nm or more, 120 nm or more, 130 nm or more, 140 nm or more, 150 nm or more, 160 nm or more, 170 nm or more, 180 nm or more, 190 nm or more, 200 nm or more; 300 nm or less, 290 nm or less, 280 nm or less, 270 nm or less, 260 nm or less, 250 nm or less, 240 nm or less, 230 nm or less, 220 nm or less, 210 nm or less, 200 nm or less not, but is not limited thereto.

According to one embodiment of the present disclosure, the oxygen gas may be collected in an amount of 1 ppm (v/w) to 35 ppm (v/w) based on the total weight of the nanoemulsion composition. More specifically, the oxygen gas may be collected in an amount of 1 ppm (v/w) or more, 5 ppm (v/w) or more, 10 ppm (v/w) or more, 15 ppm (v/w) or more, 20 ppm (v/w) or more, 21 ppm (v/w) or more, 22 ppm (v/w) or more, 23 ppm (v/w) or more, 24 ppm (v/w) or more, 25 ppm (v/w) or more, 26 ppm (v/w) or more, 27 ppm (v/w) or more, 27.1 ppm (v/w) or more; 35 ppm (v/w) or less, 34 ppm (v/w) or less, 33 ppm (v/w) or less, 32 ppm (v/w) or less, 31 ppm (v/w) or less, 30 ppm (v/w) or less, 29 ppm (v/w) or less, 28 ppm (v/w) or less, or 27.1 ppm (v/w) or less, based on the total weight of the nanoemulsion composition, but is not limited thereto.

The perfluorocarbon compound is a fully fluorine-substituted hydrocarbon compound, and the fully fluorine-substituted hydrocarbon compound refers to a hydrocarbon compound in which all hydrogen atoms are substituted with fluorine atoms. The perfluorocarbon compound is a material with very low viscosity, low surface tension, excellent spreadability, high fluidity, low dielectric constant, high vapor pressure, high compressibility and high gas solubility.

Examples of the perfluorocarbon compound may include cyclic or acyclic perfluorinated hydrocarbon, and perfluorinated aliphatic hydrocarbon or perfluorinated aromatic hydrocarbon may be included as the example. Preferably, examples of the perfluorocarbon compound may include chain fluorinated aliphatic hydrocarbon of 1 to 12 carbon atoms, and cyclic perfluorinated aliphatic hydrocarbons of 3 to 12 carbon atoms having 1 or 2 rings.

Examples of chain perfluorinated aliphatic hydrocarbon of 1 to 12 carbon atoms may include perfluorohexane, perfluoroheptane, perfluorooctane, perfluorononane, perfluorodecane, perfluoroundecane and perfluorododecane.

Examples of cyclic perfluorinated aliphatic hydrocarbon of 3 to 12 carbon atoms having 1 or 2 rings may include perfluorocyclohexane, perfluorodimethylcyclohexane, perfluoroisopropylcyclohexane, perfluorodecalin, perfluoromethyldecalin, and compounds structurally similar to these compounds.

According to one embodiment of the present disclosure, the perfluorocarbon compound may be a perfluoroalkyl halide. The perfluoroalkyl halide refers to a compound having a non-fluorine substituent, and examples thereof include perfluoroalkyl chloride, perfluoroalkyl bromide, and perfluoroalkyl iodide. The alkyl group of the perfluoroalkyl halide may have 1 to 12 carbon atoms. According to one embodiment of the present disclosure, the perfluorocarbon compound may be perfluorooctylbromide (PFOB).

According to one embodiment of the present disclosure, the perfluorocarbon compound is one or more of a chain perfluorinated aliphatic hydrocarbon of 1 to 12 carbon atoms and a cyclic perfluorinated aliphatic hydrocarbon of 3 to 12 carbon atoms having 1 or 2 rings. According to one embodiment of the present disclosure, the perfluorocarbon compound is a combination of a chain perfluorinated aliphatic hydrocarbon of 1 to 12 carbon atoms and a cyclic perfluorinated aliphatic hydrocarbon of 3 to 12 carbon atoms having 1 or 2 rings.

According to one embodiment of the present disclosure, the perfluorocarbon compound is one or more of perfluorodecalin (PFD) and perfluorohexane (PFH). According to one embodiment of the present disclosure, the perfluorocarbon compound is a combination of perfluorodecalin (PFD) and perfluorohexane (PFH).

According to one embodiment of the present disclosure, the perfluorocarbon compound is a combination of perfluorodecalin (PFD) and perfluorohexane (PFH), and the content ratio of the perfluorodecalin (PFD) and perfluorohexane (PFH) is 6:1 to 1:3 by weight. More specifically the content ratio of the perfluorodecalin (PFD) and perfluorohexane (PFH) is 6:1 or more, 5.5:1 or more, 5:1 or more, 4.5:1 or more, 4:1 or more, 3.5:1 or more, 3:1 or more; 1:3 or less, 1:2.5 or less, 1:2 or less, 1:1.5 or less, 1:1 or less, 1.5:1 or less, 2:1 or less, 2.5:1 or less, 3:1 or less by weight, but is not limited thereto. According to one embodiment of the present disclosure, the content ratio of perfluorodecalin (PFD) and perfluorohexane (PFH) is 3:1 by weight.

According to one embodiment of the present disclosure, the content of the perfluorocarbon compound may be 5% to 80% by weight based on the total weight of the nanoemulsion composition. More specifically, the content of the perfluorocarbon compound may be 5% by weight or more, 10% by weight or more, 15% by weight or more, 20% by weight or more, 25% by weight or more, 30% by weight or more, 35% by weight or more, 40% by weight or more, 45% by weight or more, 50% by weight or more, 55% by weight or more, 60% by weight or more; 80% by weight or less, 75% by weight or less, 70% by weight or less, 65% by weight or less, 60% by weight or less, based on the total weight of the nanoemulsion composition, but is not limited thereto.

According to one embodiment of the present disclosure, the oil phase part further contains one or more of phospholipid, polyglycerin stearic acid ester, and fatty acid ester of sorbitan as a main surfactant, and the nanoemulsion composition may further include one or more of cholesterol, glyceryl diester, inulin fatty acid ester, polyglycerin lauric acid ester, carboxylate salt of glutamic acid, and fatty acid ester of ethoxylated sorbitan as an auxiliary surfactant.

In the present disclosure, when a different surfactant is used, a surfactant having a relatively high emulsifying power (interfacial activity) is referred to as a "main surfactant". Compared to the case of using one type of surfactant, when mixed with the auxiliary surfactant, a synergistic effect is exhibited in that the surfactant is distributed faster and more densely in the inner phase.

According to one embodiment of the present disclosure, the total content of the auxiliary surfactant may be 0.1 to 10% by weight based on the total weight of the nanoemulsion composition. More specifically, the total content of the auxiliary surfactant may be 0.1% by weight or more, 0.2% by weight or more, 0.3% by weight or more, 0.4% by weight or more, 0.5% by weight or more, 0.6% by weight or more, 0.7% by weight or more, 0.8% by weight or more, 0.9% by weight or more, 1% by weight or more, 1.5% by weight or more, 2% by weight or more, 2.5% by weight or more, 3% by weight or more, 3.5% by weight or more, 4% by weight or more, 4.5% by weight or more, 5% by weight or more; 10% by weight or less, 9% by weight or less, 8% by weight or less, 7% by weight or less, 6% by weight or less, 5% by weight or less based on the total weight of the nanoemulsion composition, but is not limited thereto.

According to one embodiment of the present disclosure, the content ratio of the main surfactant and the auxiliary surfactant may be 10:1 to 1:3 by weight. More specifically, the content ratio may be 10:1 or more, 9.5:1 or more, 9:1 or more, 8.5:1 or more, 8:1 or more, 7.5:1 or more, 7:1 or more, 6.5:1 or more, 6:1 or more, 5.5:1 or more, 5:1 or more, 4.5:1 or more, 4:1 or more; 1:3 or less, 1:2.5 or less, 1:2 or less, 1:1.5 or less, 1:1 or less, 1.5:1 or less, 2:1 or less, 2.5:1 or less, 3:1 or less, 3.5:1 or less, 4:1 or less by weight, but is not limited thereto.

Examples of the phospholipid may include lecithin, hydrogenated lecithin, phosphatidylcholine, phosphatidylethanolamine, phosphatidylserine, and phosphatidylinositol. According to one embodiment of the present disclosure, the phospholipid is one or more selected from the group consisting of lecithin, hydrogenated lecithin and phosphatidylcholine. The phosphatidylcholine may be a naturally-derived phosphatidylcholine or a synthetic or highly purified phosphatidylcholine. According to one embodiment of the present disclosure, the phospholipid may be egg phosphatidylcholine and/or soy phosphatidylcholine.

According to one embodiment of the present disclosure, the polyglycerin stearic acid ester is one or more selected from the group consisting of polyglyceryl-10 stearate, polyglyceryl-10 isostearate, polyglyceryl-10 diisostearate, and polyglyceryl-10 distearate. According to one embodiment of the present disclosure, the polyglycerin stearic acid ester is polyglyceryl-10 stearate.

According to one embodiment of the present disclosure, the fatty acid ester of sorbitan is one or more selected from the group consisting of sorbitan monolaurate (Span 20), sorbitan monopalmitate (Span 40), sorbitan monostearate (Span 60), sorbitan monooleate (Span 80), sorbitan isostearate (Span 120).

According to one embodiment of the present disclosure, the glyceryl diester (=diglyceride, diacylglycerol) is one or more selected from the group consisting of glyceryl dilaurate, glyceryl diarachidate, glyceryl dibehenate, glyceryl dieleucate, glyceryl dihydroxystearate, glyceryl diisopalmitate, glyceryl diisostearate, glyceryl dilinoleate, glyceryl dimyristate, glyceryl dioleate, glyceryl diricinoleate, glyceryl dipalmitate, glyceryl dipalmitoliate, glyceryl distearate, glyceryl palmitate lactate, glyceryl stearate citrate, glyceryl stearate lactate and glyceryl stearate succinate. According to one embodiment of the present disclosure, the glyceryl diester is glyceryl stearate citrate.

According to one embodiment of the present disclosure, the inulin fatty acid ester is one or more selected from the group consisting of inulin octanoate, inulin decanoate, inulin laurate, inulin myristate, inulin lauryl carbamate, inulin palmitate, inulin stearate, inulin arachidate, inulin behenate, inulin oleate, inulin 2-ethylhexanoate, inulin isomyristate, inulin isopalmitate, inulin isostearate and inulin isooleate. According to one embodiment of the present disclosure, the inulin fatty acid ester is inulin lauryl carbamate.

According to one embodiment of the present disclosure, the polyglycerin lauric acid ester is one or more selected from the group consisting of polyglyceryl-2 laurate and polyglyceryl-10 laurate. According to one embodiment of the present disclosure, the polyglycerin lauric acid ester is polyglyceryl-10 laurate.

According to one embodiment of the present disclosure, the carboxylate salt of glutamic acid is one or more selected from the group consisting of sodium cocoyl glutamate, sodium lauroyl glutamate, sodium myristoyl glutamate, sodium palmitoyl glutamate, sodium stearoyl glutamate, disodium cocoyl glutamate, disodium stearoyl glutamate, potassium cocoyl glutamate, potassium lauroyl glutamate, and potassium myristoyl glutamate. According to one embodiment of the present disclosure, the carboxylate salt of glutamic acid is sodium stearoyl glutamate.

According to one embodiment of the present disclosure, examples of the fatty acid ester of ethoxylated sorbitan may include PEG-20 sorbitan monolaurate (Tween 20), PEG-4 sorbitan monolaurate (Tween 21), PEG-20 sorbitan monopalmitate (Tween 40), PEG-20 sorbitan monostearate (Tween 60), PEG-4 sorbitan monostearate (Tween 61), PEG-20 sorbitan monooleate (Tween 80). According to one embodiment of the present disclosure, the nonionic surfactant may be Tween 80.

According to one embodiment of the present disclosure, at a time point at least 10 seconds after the start of dissolution of the composition, the oxygen gas concentration may reach equilibrium with the system (e.g., when the composition is in contact with the atmospheric layer, the system may be the atmospheric layer). Therefore, oxygen gas can be released for more than 10 seconds until equilibrium is reached. More specifically, oxygen gas can be released for 10 seconds or more, 20 seconds or more, 30 seconds or more, 40 seconds or more, 50 seconds or more, 1 minute or more, 3 minutes or more, 5 minutes or more, 10 minutes or more, 30 minutes or more, 1 hour or more, 2 hours or more, 3 hours or more, 4 hours or more, 5 hours or more, 6 hours or more, 7 hours or more, 8 hours or more, 9 hours or more, 10 hours or more, 20 hours or more, 30 hours or more, 32 hours or more, 34 hours or more, 36 hours or more, 38 hours or more, 40 hours or more, 42 hours or more, 44 hours or more, 46 hours or more, 48 hours or more, 50 hours or more, 60 hours or more, 70 hours or more, 80 hours or more, 90 hours or more, 100 hours or more, 110 hours or more, 120 hours or more, 130 hours or more, 140 hours or more, but is not limited thereto.

The term "equilibrium" refers to a state in which the oxygen gas transfer rate between the composition of the present disclosure and the system in contact with the composition is the same, so that the amount of oxygen gas in the composition is maintained at a constant level. In order for the oxygen gas concentration of the composition to reach equilibrium with the system, or even after it is reached, the time for continuously releasing oxygen gas into the system may be 1 minute or more by the sustained release of oxygen gas from the nanoemulsion of the present disclosure.

According to one embodiment of the present disclosure, the composition may be a composition for preventing hair loss or promoting hair growth.

The term "hair loss" may refer to absence of hair on the part where hair is normally present, for example, it may mean depilation of hair from the scalp. In addition, the term "promoting hair growth" may refer to the healthy growth of existing hair as well as the promotion of growth of new hair.

The hair loss prevention or hair growth promotion may be due to the proliferation of hair follicle cells or hair growth. Specifically, the proliferation of the hair follicle cells means the proliferation of dermal papilla cells or hair germinal matrix cells. The "dermal papilla cells" are skin cells surrounding the hair follicle and may refer to cells that play an important role in hair growth. The "hair germinal matrix cells" refers to cells existing in the dermal papilla tissue and capable of producing hair. Specifically, the hair growth means that the dermal papilla, which is supplied with nutrients and oxygen from the capillaries, delivers nutrients and various growth factors, growth signals, etc. to the hair germinal matrix cells, while the hair germinal matrix cells divide. Therefore, in preventing hair loss or promoting hair growth, the supply of nutrition and oxygen to the dermal papilla cells and/or hair germinal matrix cells is an important factor. The present disclosure has been devised from the above, and an object of the present disclosure is to provide a composition capable of preventing hair loss or promoting hair growth by increasing the amount of oxygen supplied to the hair bulb.

According to one embodiment of the present disclosure, the composition may further include an additional active ingredient for hair loss prevention or hair growth promotion. The active ingredient is a component capable of exhibiting an effect of preventing hair loss or promoting hair growth, and the type of the active ingredient is not limited as long as it is a component capable of inhibiting the activity of prostaglandin E2 (PGE2) that can prevent the activity inhibitory effect on 5-alpha-reductase, which is known as the main cause of hair loss, and hair loss caused by scalp inflammation.

According to one embodiment of the present disclosure, the composition may be a formulation for external application to skin. The term "skin" refers to a tissue covering the body surface of an animal, and is the broadest concept including not only tissues covering body surfaces such as the face or body, but also scalp and hair.

According to one embodiment of the present disclosure, the composition may be a cosmetic, pharmaceutical or food composition.

Specifically, in the cosmetic composition, the formulation is not particularly limited, and according to one embodiment of the present disclosure, the composition may be formulated by a commonly used method. For formulation, reference may be made to the contents disclosed in the International Cosmetic Ingredient Dictionary (INCI) published by the Cosmetic, Toiletry and Fragrance Association.

Specifically, the composition may be formulated as a hair rinse, a shampoo, a hair conditioner, a hair pack, a hair oil, a hair treatment, a hair cream, a hair lotion, a hair gel, a hair essence, a hair spray, a hair serum, a hair ampoule, an emulsion, cream, an essence, etc. The formulation may be of a rinse-off type or a wash-off type, meaning that the formulation is rinsed after application to the hair. Alternatively, it can be of a leave-on or leave-in type, meaning that the formulation remains on the hair after application.

The composition may additionally contain fatty substances, organic solvents, solubilizers, thickening agents, gelling agents, emollients, antioxidants, suspending agents, stabilizers, foaming agents, fragrances, surfactants, antiseptics, pH controllers, water, ionic or nonionic emulsifiers, fillers, sequestering agents, chelating agents, preservatives, blocking agents, wetting agents, essential oils, dyes, pigments, hydrophilic or lipophilic active agents, adjuvants commonly used in the field of cosmetology or dermatology, such as any other ingredients commonly used in cosmetics, as needed.

When the formulation of the cosmetic composition is a solution or emulsion, a solvent, solubilizer or emulsifier is used as a carrier component. As examples, there are water, ethanol, isopropanol, ethyl carbonate, ethyl acetate, benzyl alcohol, benzyl benzoate, propylene glycol, 1,3-butylglycol oil, glycerol fatty ester, polyethylene glycol or fatty acid ester of sorbitan.

When the formulation of the cosmetic composition is a suspension, a liquid diluent such as water, ethanol or propylene glycol, a suspending agent such as ethoxylated isostearyl alcohol, polyoxyethylene sorbitol ester, and polyoxyethylene sorbitan ester, crystalline cellulose, aluminum metahydroxide, bentonite, agar, tracanth, etc. may be used as a carrier component.

When the formulation of the cosmetic composition is a paste, a cream or a gel, animal oil, vegetable oil, wax, paraffin, starch, tracanth, cellulose derivative, polyethylene glycol, silicone, bentonite, silica, talc, zinc oxide and the like may be used as a carrier component.

The cosmetic composition may additionally contain a thickening agent. As the thickening agent included in the cosmetic composition, methyl cellulose, carboxy methyl cellulose, carboxy methyl hydroxy guanine, hydroxy methyl cellulose, hydroxy ethyl cellulose, carboxy vinyl polymer, polyquaternium, cetearyl alcohol, stearic acid, carrageenan and the like may be used, and preferably, one or more of carboxymethyl cellulose, carboxyvinyl polymer, and polyquaternium may be used, and most preferably, carboxyvinyl polymer may be used.

The cosmetic composition may contain various suitable bases and additives as needed, and the types and amounts of these components can be easily selected by the inventor. If necessary, it may contain acceptable additives, for example, may further include components such as preservatives, pigments, and additives commonly used in the art. Specifically, the preservative may be phenoxyethanol or 1,2-hexanediol, and the fragrance may be an artificial fragrance.

The cosmetic composition may include a composition selected from the group consisting of water-soluble vitamin, oil-soluble vitamin, high-molecular peptide, high-molecular polysaccharide, sphingolipid, and seaweed extract. As other ingredients that may be added, there may be an oil and fat, a moisturizer, an emollient, a surfactant, an organic and inorganic pigment, an organic powder, an UV absorber, an antiseptic, a bactericide, antioxidant, a plant extract, a pH controller, an alcohol, a colorant, a fragrance, a blood circulation stimulant, a cooling agent, an antiperspirant, purified water, etc. In addition, the ingredients that may be contained in the cosmetic composition are not limited thereto and, the amount of the ingredients may be determined within a range not negatively affecting the purpose and effect of the present disclosure.

In the pharmaceutical composition, the pharmaceutical composition may be in various formulations, such as oral or parenteral formulation. Usually, the pharmaceutical composition is prepared into a formulation using a commonly used diluent or excipient such as a filler, an extender, a binder, a wetting agent, a disintegrant, a surfactant, etc. Solid formulations for oral administration may include a tablet, a pill, a powder, a granule, a soft or hard capsule, etc. The solid formulation is prepared by mixing at least one compound with at least one excipient, e.g., starch, calcium carbonate, sucrose, lactose, gelatin, etc. In addition to the simple excipient, a lubricant such as magnesium stearate, talc, etc. may also be used. Liquid formulations for oral administration may include a suspension, a liquid medicine for internal use, an emulsion, a syrup, etc. In addition to a commonly used simple diluent such as water or liquid paraffin, various excipients such as a humectant, a sweetener, an aromatic, a preservative, etc. may also be contained. Formulations for parenteral administration may include a sterilized aqueous solution, a nonaqueous solution, a suspension, an emulsion, a freeze-dried product and a suppository. The nonaqueous solution or suspension may contain propylene glycol, polyethylene glycol, vegetable oil such as olive oil, an injectable ester such as ethyl oleate, etc. As a base of the suppository, witepsol, macrogol, tween 61, cocoa butter, laurin butter, glycerogelatin, etc. may be used.

The pharmaceutical dosage form of the pharmaceutical composition may be used alone or in combination with other pharmaceutically active compounds, as well as in an appropriate set. The salt is not particularly limited as long as it is pharmaceutically acceptable. For example, a hydrochloride, a sulfate, a nitrate, a phosphate, a hydrofluoride, a hydrobromide, a formate, an acetate, a tartrate, a lactate, a citrate, a fumarate, a maleate, a succinate, a methanesulfonate, a benzenesulfonate, a toluenesulfonate, a naphthalenesulfonate, etc. may be used.

The pharmaceutical composition may be administered parenterally or orally depending on purposes and the pharmaceutical composition may be administered once or several times a day such that a daily dosage is to be 0.1 to 500 mg, specifically 1 to 100 mg, per kg body weight. The administration dosage for a particular patient may vary depending on the body weight, age, sex, health status, and diet of a patient, administration time, administration method, excretion rate, severity of disease, etc.

The pharmaceutical composition may be prepared into any formulation suitable for a pharmaceutical composition, including an oral formulation such as a powder, a granule, a tablet, a soft or hard capsule, a suspension, an emulsion, a syrup, an aerosol, etc., a formulation for external application to skin such as an ointment, a cream, etc., a suppository, an injection, a sterile injectable solution, etc., according to a commonly used method. Specifically, it may be prepared into an injection or a formulation for external application to skin.

The pharmaceutical composition may be administered to a mammal such as rat, mouse, livestock, human, etc. through various routes including parenteral and oral routes. Any mode of administration may be expected. For example, it may be administered orally, transdermally, intravenously, intramuscularly or subcutaneously. The pharmaceutical composition may be administered through various routes that can be easily adopted by those skilled in the art. In particular, the pharmaceutical composition may be administered as a formulation for external application to skin by applying onto the skin surface.

In the food composition, the food composition may be a health functional food composition. The formulation of the food composition is not particularly limited. For example, it may be formulated into a tablet, a granule, a powder, a liquid formulation such as a drink, a caramel, a gel, a bar, etc. The food composition of each formulation may contain, in addition to the active ingredient, various ingredients that are commonly used in the related art and can be appropriately selected by those skilled in the art without difficulty depending on the formulation or purpose of use. A synergistic effect may occur when applied simultaneously with other raw materials.

In the food composition, the determination of the administration dose of the active ingredient is within the level of those skilled in the art. A daily dose may be, for example, 0.1 mg/kg/day to 5000 mg/kg/day, more specifically 50 mg/kg to 500 mg/kg/day, but is not limited thereto. The administration dose will vary depending on various factors such as age, health status, and complications of the subject to be administered.

The food composition, for example, may be various foods such as a chewing gum, a caramel product, a candy, a frozen dessert, confectionery, etc., drink products such as a soft drink, mineral water, an alcoholic beverage, etc. or health functional foods including a vitamin and a mineral.

The food composition may contain various nutrients, vitamins, minerals (electrolytes), flavoring agents including synthetic and natural flavoring agents, colorants, extenders (cheese, chocolate, etc.), pectic acid and salts thereof, alginic acid and salts thereof, organic acids, protective colloidal thickeners, pH controllers, stabilizers, preservatives, glycerin, alcohols, carbonating agents used in soft drinks, etc. The functional food composition may contain a pulp for preparing a natural fruit juice, a fruit drink or a vegetable drink. These ingredients may be used either independently or in combination. The mixing ratio of the additives is of no significant importance. In an aspect of the present disclosure, the additives may be contained in an amount of about 0 to 20 parts by weight based on 100 parts by weight of the composition.

In another aspect, the present disclosure provides a method for preparing the composition including the steps of preparing a first mixture by mixing water; oil; one or more of phospholipid and fatty acid ester of sorbitan; and a nonionic surfactant; preparing a second mixture by adding a perfluorocarbon compound to the first mixture; preparing a crude emulsion by homogenizing the second mixture; and bubbling oxygen in the crude emulsion.

A buffer solution may be further mixed in the step of preparing the first mixture. Examples of the buffer may include 4-(2-hydroxyethyl)-1-piperazineethanesulfonic acid (HEPES), 2-(N-morpholino)ethanesulfonic acid (MES), phosphated buffered saline (PBS), tris(2-amino-2 hydroxymethyl propane-1,3-diol (THAM), phosphate buffer (PB), 3-(N-morpholino)propanesulfonic acid (MOPS).

The "homogenization" may include fluidization. The homogenization may include ultrasonic homogenization and high-pressure homogenization. The high-pressure homogenization may be performed under a pressure of 500 to 2500 bar.

For the components mentioned in the preparation method, the same contents as those related to the composition may be applied.

As another aspect, the present disclosure provides the use of a water phase part containing water; and an oil phase part dispersed in the water phase part and made of nanoparticle containing a perfluorocarbon compound in preparing a nanoemulsion composition for preventing hair loss or promoting hair growth. The oil phase part includes oxygen gas, and the oxygen gas is released in sustained release.

As another aspect, the present disclosure provides a method for preventing hair loss or promoting hair growth, including the steps of applying to an individual in need thereof a nanoemulsion composition including a water phase part containing water and an oil phase part dispersed in the water phase part and made of nanoparticle containing a perfluorocarbon compound. The oil phase part contains oxygen gas, and the oxygen gas is released in sustained release.

As another aspect, the present disclosure provides a water phase part containing water and an oil phase part dispersed in the water phase part and made of nanoparticle containing a perfluorocarbon compound, which are used in preventing hair loss or promoting hair growth. The oil phase part contains oxygen gas, and the oxygen gas is released in sustained release.

EXAMPLES

Hereinafter, the present disclosure will be described in detail by way of examples. However, the following examples are only examples to help the overall understanding of the present disclosure, and the content of the present disclosure is not limited to the following examples.

<Preparation Example 1> Preparation of Oxygen Sustained Release Nanoparticles

Water; oleyl polyoxyl-6 glyceride and propylene glycol monocaprylate (Gatefosse, Saint-Priest, France); egg phosphatidylcholine or soy phosphatidylcholine (Lipoid, Ludwigshafen, Germany); and Tween 80 or Poloxamer 188 (Merck, Darmstadt, Germany) were dissolved in PBS (pH 7.4) and stirred at room temperature for 30 minutes using a magnetic stirrer. PFOB (Sinquest Laboratories, FL, USA) was then added to the mixture and stirred for 30 minutes. The mixture was homogenized at 8100 rpm for 30 seconds in a high-speed homogenizer (HG-15A; Daehan Science, Wonju, Korea) to obtain a crude emulsion, and then treated in an LV1-30K microfluidics (Microfluidics, Westwood, Massachusetts, USA) at 15,000 psi (about 1034 bar) for 5 cycles. Next, oxygen was bubbled into the crude emulsion at a rate of 1 mL/min to prepare a nanoemulsion containing oxygen gas.

<Test Example 1> Size Evaluation of Nanoemulsion According to the Type and Content Ratio of Main Surfactant and Auxiliary Surfactant 1. Material Preparation A nanoemulsion composition was prepared according to the composition of Table 1 below. The content of each ingredient was expressed as a relative content ratio, and the unit was weight %.

TABLE 1

| Category | PFOB | Egg phosphatidylcholine | Span 80 | Tween 80 | Poloxamer 188 | Water |
|---|---|---|---|---|---|---|
| Example 1 | 10 | 5 | — | — | — | to 100 |
| Example 2 | 10 | 3.75 | — | — | 1.25 | to 100 |
| Example 3 | 10 | 2.5 | — | — | 2.5 | to 100 |
| Example 4 | 10 | 1.25 | — | — | 3.75 | to 100 |
| Example 5 | 10 | — | — | — | 5 | to 100 |
| Example 6 | 10 | 5 | — | — | — | to 100 |
| Example 7 | 10 | 3.75 | — | 1.25 | — | to 100 |
| Example 8 | 10 | 2.5 | — | 2.5 | — | to 100 |
| Example 9 | 10 | 1.25 | — | 3.75 | — | to 100 |
| Example 10 | 10 | — | — | 5 | — | to 100 |
| Example 11 | 10 | — | 5 | — | — | to 100 |
| Example 12 | 10 | — | 3.75 | — | 1.25 | to 100 |
| Example 13 | 10 | — | 2.5 | — | 2.5 | to 100 |
| Example 14 | 10 | — | 1.25 | — | 3.75 | to 100 |
| Example 15 | 10 | — | — | — | 5 | to 100 |
| Example 16 | 10 | — | 5 | — | — | to 100 |
| Example 17 | 10 | — | 3.75 | 1.25 | — | to 100 |
| Example 18 | 10 | — | 2.5 | 2.5 | — | to 100 |
| Example 19 | 10 | — | 1.25 | 3.75 | — | to 100 |
| Example 20 | 10 | — | — | 5 | — | to 100 |

2. Evaluation Method of Nanoemulsion Size

The particle size and surface charge of the prepared nanoemulsion were measured and evaluated using a zeta potential/particle size analyzer (ELSZ-2000 series, Otsuka Electronics, Japan). The measurement was performed by diluting the nanoemulsion sample for evaluation with phosphate buffered saline (PBS; Corning, USA) and then putting the diluted nanoemulsion sample into the analyzer. The result was shown in FIG. 1 (unit: nm).

3. Evaluation Result of Nanoemulsion Size

With respect to the types of the main surfactant and the auxiliary surfactant, when Poloxamer 188 was used as the auxiliary surfactant, it was confirmed from FIG. 1 that an emulsion having a diameter exceeding 1000 nm, not in nano units, was produced. Thus, it can be seen that the use of Tween 80 as the auxiliary surfactant is particularly preferred.

<Test Example 2> Particle Size Evaluation of a Nanoemulsion Composition According to the Content Ratio of Main Surfactant and Auxiliary Surfactant The following test was performed to evaluate the particle size change of the nanoemulsion composition according to the content of PFOB.

1. Material Preparation

A nanoemulsion composition was prepared according to the composition of Table 2 below. The content of each ingredient was expressed as a relative content ratio, and the unit was weight %.

TABLE 2

| Category | PFOB | Soy phosphatidyl-choline | Span 80 | Tween 80 | Water |
|---|---|---|---|---|---|
| Example 21 | 40 | 1.88 | — | 0.63 | to 100 |
| Example 22 | 40 | — | 1.88 | 0.63 | to 100 |
| Example 23 | 40 | 3.75 | — | 1.25 | to 100 |
| Example 24 | 40 | — | 3.75 | 1.25 | to 100 |
| Example 25 | 50 | 1.88 | — | 0.63 | to 100 |
| Example 26 | 50 | — | 1.88 | 0.63 | to 100 |
| Example 27 | 50 | 3.75 | — | 1.25 | to 100 |
| Example 28 | 50 | — | 3.75 | 1.25 | to 100 |

TABLE 2-continued

| Category | PFOB | Soy phosphatidyl-choline | Span 80 | Tween 80 | Water |
|---|---|---|---|---|---|
| Example 29 | 60 | 1.88 | — | 0.63 | to 100 |
| Example 30 | 60 | — | 1.88 | 0.63 | to 100 |
| Example 31 | 60 | 3.75 | — | 1.25 | to 100 |
| Example 32 | 60 | — | 3.75 | 1.25 | to 100 |
| Example 33 | 7.5 | 3.75 | — | 1.25 | to 100 |
| Example 34 | 15 | 3.75 | — | 1.25 | to 100 |
| Example 35 | 30 | 3.75 | — | 1.25 | to 100 |

2. Evaluation Method of the Particle Size of a Nanoemulsion Composition

The particle size and surface charge of the prepared nanoemulsion were measured and evaluated using a zeta potential/particle size analyzer (ELSZ-2000 series, Otsuka Electronics, Japan). The measurement was performed by diluting the nanoemulsion sample for evaluation with phosphate buffered saline (PBS; Corning, USA) and then putting the diluted nanoemulsion sample into the analyzer. The result was shown in Table 3 (unit: nm).

TABLE 3

| Category | Average particle diameter |
|---|---|
| Example 21 | 179.61 ± 9.30 |
| Example 22 | 209.92 ± 7.09 |
| Example 23 | 165.82 ± 8.88 |
| Example 24 | 139.92 ± 7.09 |

TABLE 3-continued

| Category | Average particle diameter |
| --- | --- |
| Example 25 | 210.43 ± 5.82 |
| Example 26 | 204.12 ± 11.65 |
| Example 27 | 182.40 ± 9.77 |
| Example 28 | 144.12 ± 11.65 |
| Example 29 | 251.6 ± 2.96 |
| Example 30 | 195.28 ± 8.08 |
| Example 31 | 200.64 ± 4.26 |
| Example 32 | 135.28 ± 8.08 |
| Example 33 | 200.64 ± 4.26 |
| Example 34 | 200.64 ± 4.26 |
| Example 35 | 200.64 ± 4.26 |

3. Evaluation Result of the Particle Size of a Nanoemulsion Composition

It was confirmed from Table 3 that even when PFOB was contained in a relatively high content of 60% (w/v), the nanoemulsion of a desirable size was produced. On the other hand, when soy phosphatidylcholine was used as the main surfactant, it was confirmed that the size of the nanoemulsion was reduced as the content of PFOB was increased. When Span 80 was used as the main surfactant, it was confirmed that the size of the nanoemulsion increased as the content of PFOB increased.

<Test Example 3> Evaluation of the Oxygen Encapsulation Rate of a Nanoemulsion Composition According to the Content of a Perfluorocarbon Compound 1. Material Preparation The nanoemulsion compositions of Examples 31 and 33 to 35 were prepared as the content of PFOB was 60% by weight, 7.5% by weight, 15% by weight, and 30% by weight, respectively.

2. Evaluation Method of the Oxygen Encapsulation Rate of the Nanoemulsion Composition The oxygen concentration in the nanoemulsion was evaluated using a Fospor-R oxygen sensor (Ocean Optics, USA). A Fospor-R oxygen sensor probe was placed in a container containing the nanoemulsion solution to measure the oxygen concentration in real time. The result was shown in FIG. 2 (unit: ppm (v/w)).

3. Evaluation Result of the Oxygen Encapsulation Rate of Nanoemulsion

Figure 2:
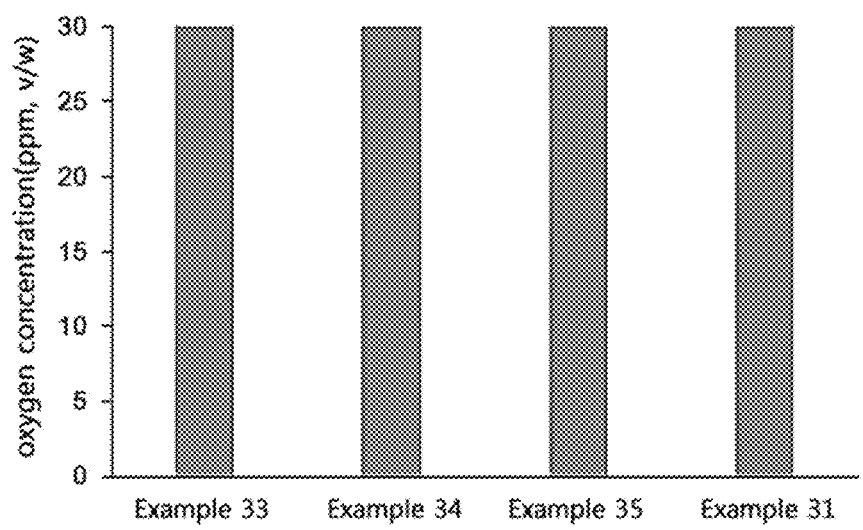
FIG. 2 is a graph showing an oxygen encapsulation rate of nanoemulsion according to the content of a perfluorocarbon compound.

It was confirmed from FIG. 2 that oxygen of 30 ppm (v/w) or more was encapsulated in all of the nanoemulsions of Example 31 and Examples 33 to 35.

<Test Example 4> Evaluation of the Oxygen Release Rate of a Nanoemulsion Composition According to the Content of a Perfluorocarbon Compound 1. Material Preparation The nanoemulsion compositions of Example 31 and Examples 33 to 35 used in Test Example 3 were used.

2. Evaluation Method of the Oxygen Release Rate of a Nanoemulsion Composition

Figure 3:
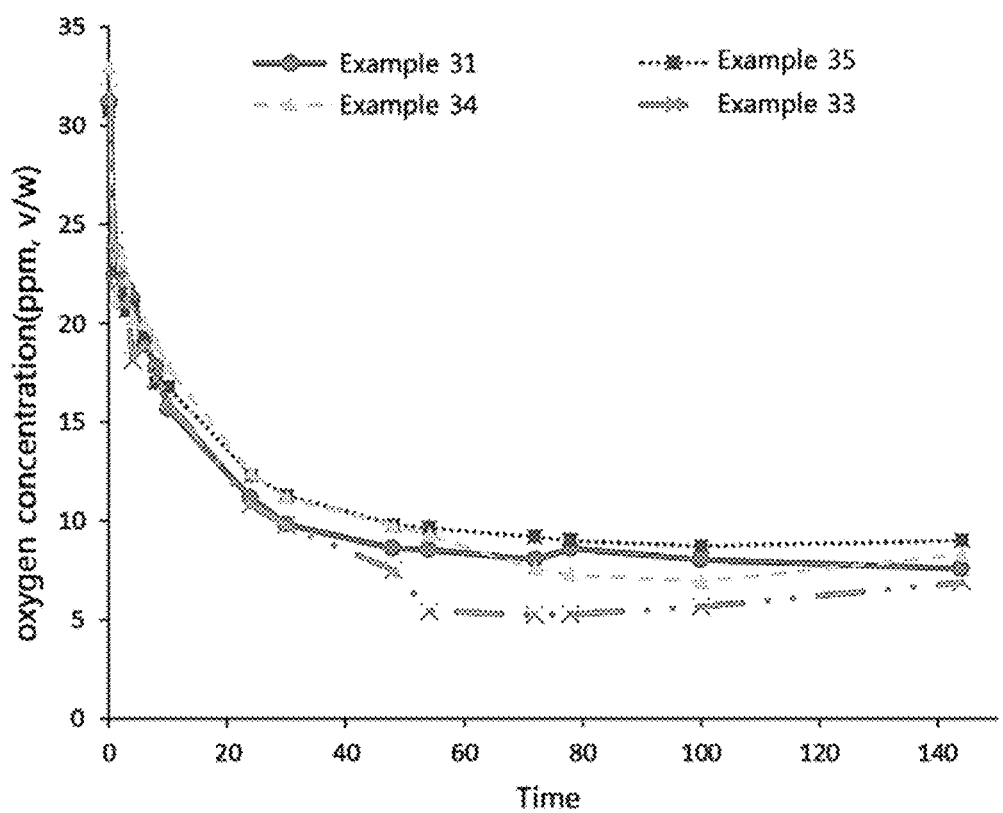
FIG. 3 is a graph showing an oxygen release degree of nanoemulsion according to the content of a perfluorocarbon compound.

The oxygen-encapsulated nanoemulsion was stored in a cell incubator fixed at 37° C., and the oxygen concentration was measured in real time using a Fospor-R oxygen sensor (Ocean Optics, USA) at a set time interval. The result was shown in FIG. 3 (unit: ppm (v/w)).

3. Evaluation Result of the Oxygen Release Rate of Nanoemulsion

In water used in a general industrial or home boiler, about 8 ppm of oxygen was dissolved at a temperature of 20° C. It was confirmed from FIG. 3 that the nanoemulsion compositions of Examples 31 and 33 to 35 all continued to release oxygen until about 40 hours to reach an equilibrium state, and from thereafter, until 140 hours which was the measurement time, maintained an oxygen concentration exceeding 8 ppm, which was the equilibrium state of the amount of dissolved oxygen.

<Reference Example 1> Culturing of Dermal Papilla Cells

Using a medium containing 10% fetal bovine serum (Gibco, USA) and 5% penicillin/streptomycin (Invitrogen, USA) in DMEM (Dulbecco's Modified Eagle's Medium) as a culture medium, human follicle dermal papilla cells (HFDPC, cat #C-12071; Promo Cell, USA) were cultured in a 5% carbon dioxide incubator at 37° C. for 1 day, then the medium was exchanged and cultured again for two days. Thereafter, the cells were cultured while exchanging with a new medium every two days.

<Test Example 5> Cytotoxicity Test

1. Evaluation Method of Cytotoxicity

After the dermal papilla cells cultured in Reference Example 1 were newly cultured in a 96 well dish for one day, the cultured cells were treated with the nanoemulsion composition of Example 31 in which oxygen was captured at a concentration of 0 ppm to 2000 ppm and Example 1 in which oxygen was not captured as a control at a concentration of 0 ppm to 2000 ppm, respectively. After incubation for 24 hours and 72 hours, cell viability was confirmed by measuring absorbance at 450 nm using the QuantiMax WST-8 Cell viability assay kit. The result was shown in FIG. 4 (unit: %).

2. Evaluation Result of Cytotoxicity

Figure 4:
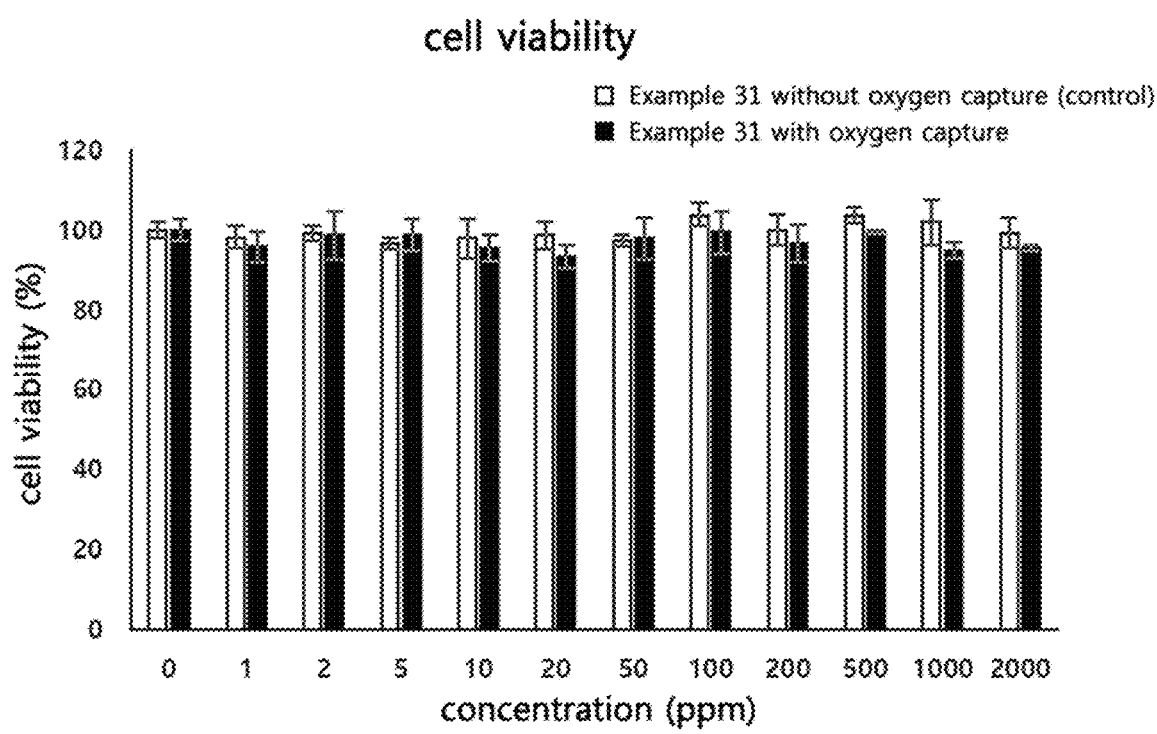
FIG. 4 is a graph showing the evaluation result of cytotoxicity.

Like the control in which oxygen was not captured, even when the nanoemulsion composition of Example 31 in which oxygen was collected was treated, it did not have any effect on the cells as shown in FIG. 4. From this, it was confirmed that the nanoemulsion composition of Example 31 had no toxicity to cells and was safe.

<Test Example 6> Evaluation of Change in Oxygen Level by Nanoemulsion

1. Evaluation Method of Change in Oxygen Level

After removing the medium from the dermal papilla cells cultured in Reference Example 1, under extreme hypoxia conditions, the cells were treated with Example 31 in which oxygen was captured and the nanoemulsion composition of Example 31 in which oxygen was not captured as a control, respectively. The oxygen concentration in the medium was measured using a NeoFox fluorometer (Ocean Optics, Dunedin, Florida, USA) equipped with a Fospor-R oxygen sensor while culturing for 24 hours. The result was shown in FIG. 5 (unit: %).

2. Evaluation Result of Cytotoxity

Figure 5:
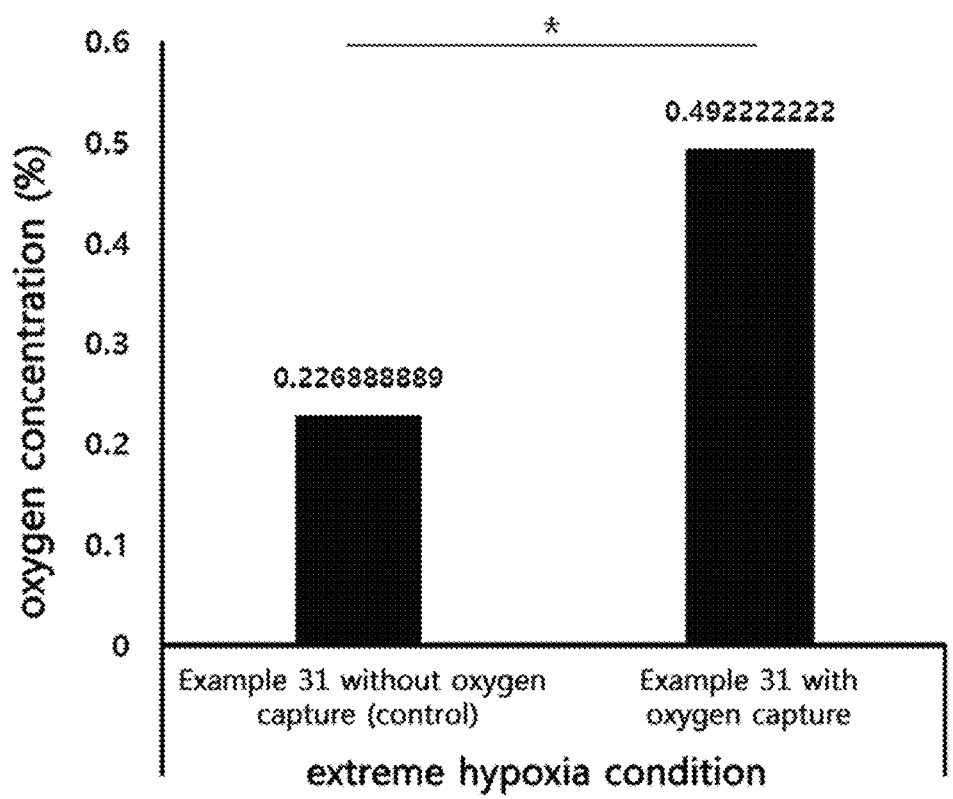
FIG. 5 is a graph showing an oxygen level change by nanoemulsion.

It was confirmed from FIG. 5 that the oxygen concentration of the control group in which oxygen was not captured was 0.227%, whereas when the nanoemulsion composition of Example 31 in which oxygen was captured was treated, the oxygen concentration increased to 0.492%. From this, it can be seen that when the nanoemulsion composition of Example 31 is treated, it can be converted from an extreme-hypoxia condition to a condition in which oxygen of a certain level or more is supplied.

<Test Example 7> Cell Growth Evaluation

1. Cell Growth Evaluation Method

After removing the medium from the dermal papilla cells cultured in Reference Example 1, under the conditions and treatments of Table 4 below, the cells were treated with Example 1 in which oxygen was captured and the nanoemulsion composition in which oxygen was not captured as a control, respectively. Cells were treated with the nanoemulsion composition of Example 31 in which oxygen was captured at concentrations of 100 ppm and 200 ppm, respectively.

TABLE 4

| Category | Conditions | Addition of serum (10%) | Treated nanoemulsion |
|---|---|---|---|
| Example 1 | Extreme hypoxia | ◯ | Control |
| Example 2 | Extreme hypoxia | X | Control |
| Example 3 | Extreme hypoxia | ◯ | Oxygen nano-emulsion 100 ppm |
| Example 4 | Extreme hypoxia | X | Oxygen nano-emulsion 100 ppm |
| Example 5 | Extreme hypoxia | ◯ | Oxygen nano-emulsion 200 ppm |
| Example 6 | Extreme hypoxia | X | Oxygen nano-emulsion 200 ppm |
| Example 7 | hypoxia | ◯ | Control |
| Example 8 | hypoxia | X | Control |
| Example 9 | normoxia | ◯ | Control |
| Example 10 | normoxia | X | Control |

The growth degree of dermal paplilla cells was confirmed using an optical microscope (Nikon Eclipse T100, Japan). The image was shown in FIG. 6, and a graph showing the quantification of the number of cells was shown in FIG. 7 (unit: %).

2. Evaluation Result of Cell Growth

Figure 6:
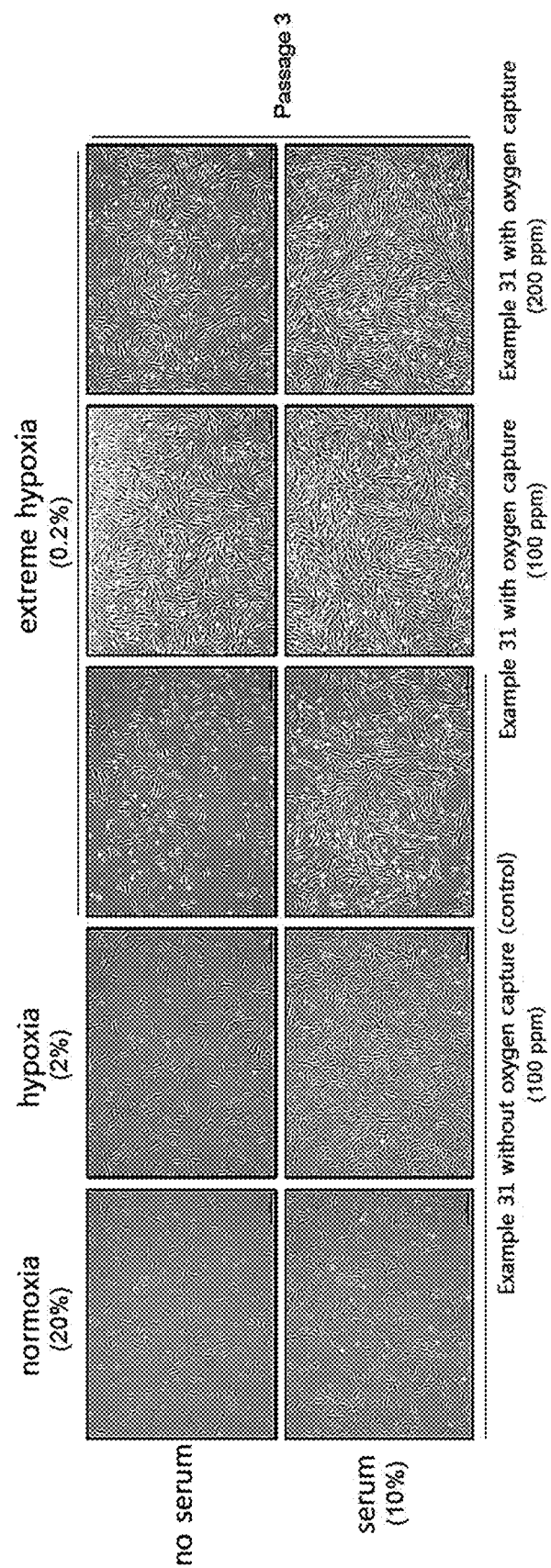
FIG. 6 is an image showing cell growth evaluation result.
Figure 7:
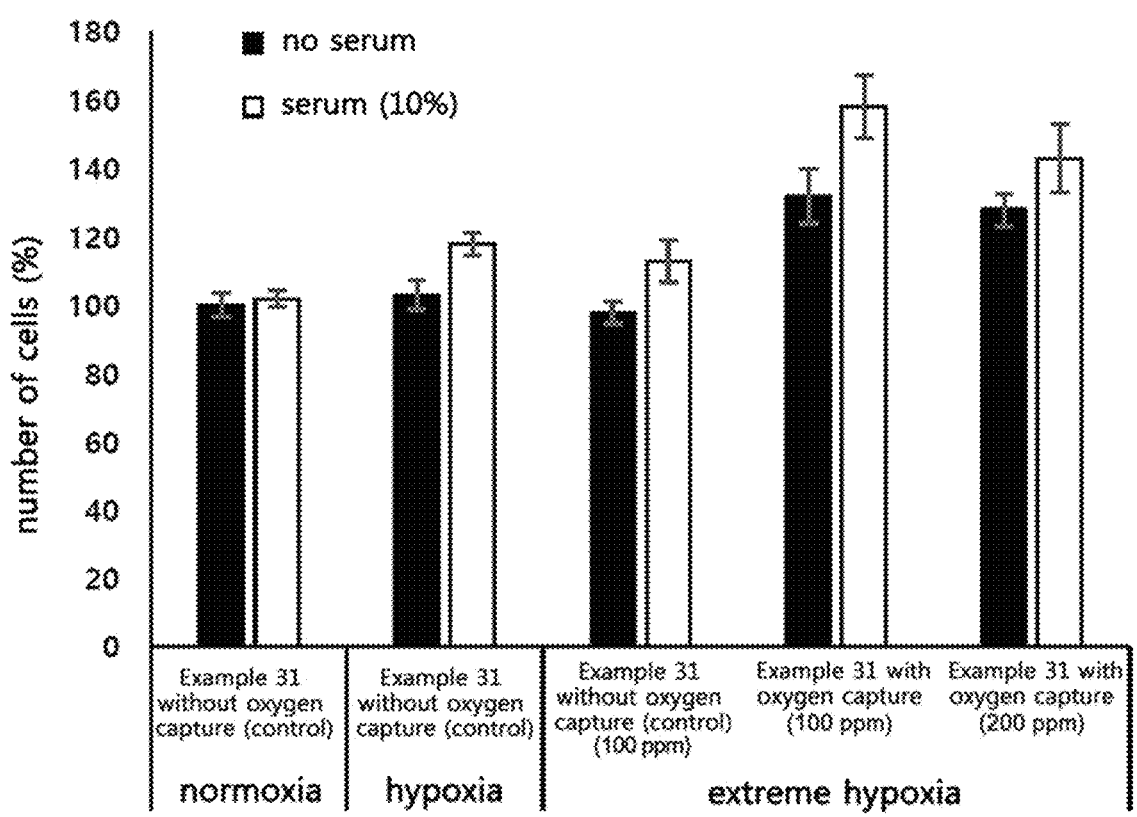
FIG. 7 is a graph showing the quantification of cell growth evaluation result.

It was confirmed from FIGS. 6 and 7 that for the growth of dermal papilla cells, it was more effective to supply oxygen rather than the presence of serum. In addition, it was confirmed that compared to the treatment with the nanoemulsion composition in which oxygen was captured at a concentration of 200 ppm, when the nanoemulsion composition in which oxygen was captured at a concentration of 100 ppm was treated, better cell growth ability was exhibited.

<Test Example 8> Hair Follicle Growth Evaluation

1. Evaluation Method of Hair Follicle Growth

Hair follicle samples to be applied to the experiment were isolated from humans. The isolated hair follicle samples were placed in a 24-well plate (Nunc, Wiesbaden, Germany) and cultured in DMEM medium containing 2 mM L-glutamine (PAA, Coelbe, Germany), 10 µg/ml insulin, 10 ng/ml hydrocortisone (Sigma, St Louis, MO), 100 u/ml Penicillin/streptomycin (Gibco, NY, USA) at 3 to 5 samples per well.

Under extreme hypoxia conditions, the nanoemulsion in which oxygen was captured at a concentration of 100 ppm and the nanoemulsion composition in which oxygen was not captured as a control were treated in the 24-well plate, respectively. A sample without any treatment was used as a negative control. The medium was changed every 2 to 3 days. The hair follicles were photographed using a stereo microscope (Olympus SZX16, Japan), and the hair growth length was measured using the Image J program, and the image was shown in FIG. 8. A graph showing the quantification of hair growth length was shown in FIG. 9 (unit: µm).

2. Evaluation Result of Hair Follicle Growth

Figure 8:
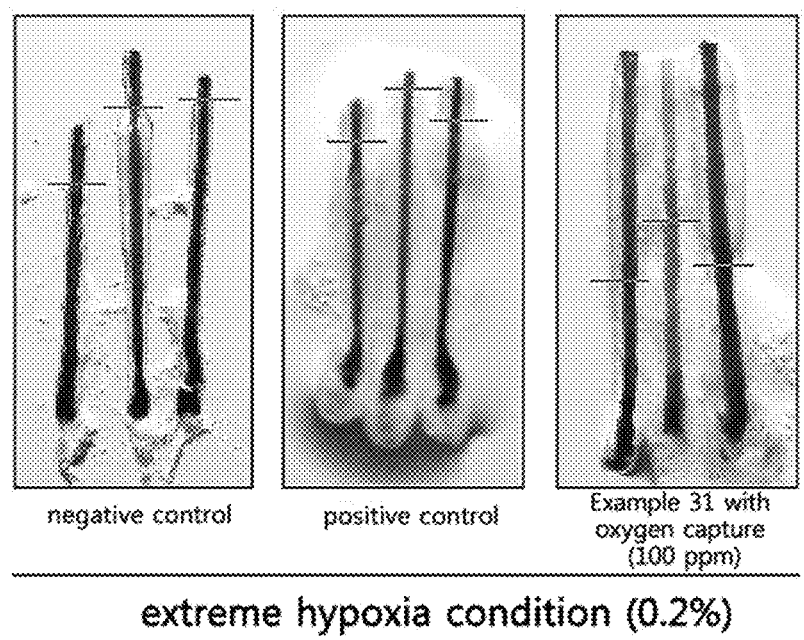
FIG. 8 is an image showing the evaluation result of hair follicle growth.
Figure 9:
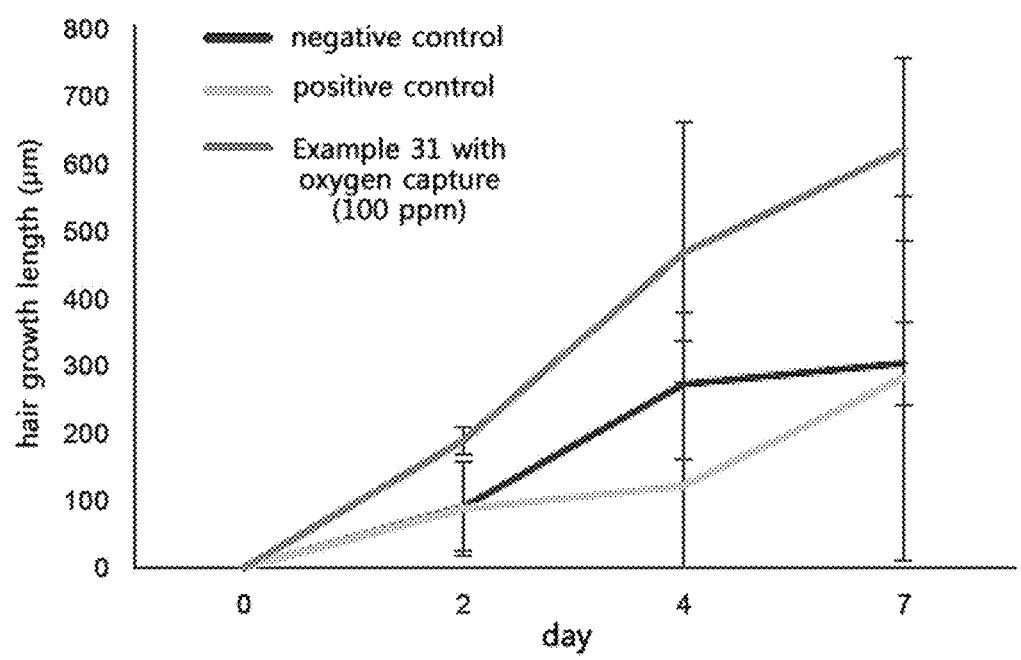
FIG. 9 is a graph showing the quantification of the evaluation result of hair follicle growth.

It was confirmed from FIGS. 8 and 9 that when the nanoemulsion composition in which oxygen was captured at a concentration of 100 ppm was treated, the hair follicle length growth ability was statistically significant.

<Preparation Example 2> Preparation of Oxygen Sustained Release Nanoparticles

Water; oleyl polyoxyl-6 glyceride and propylene glycol monocaprylate (Gatefosse, Saint-Priest, France); soy phosphatidylcholine (Lipoid, Ludwigshafen, Germany); and Tween 80 (Merck, Darmstadt, Germany) were dissolved in PBS (pH 7.4) and stirred at room temperature for 30 minutes using a magnetic stirrer.

Then, PFOB (Sinquest Laboratories, FL, USA), BB61 (70-95% perfluorohexane, 1-20% perfluorodecalin and 1-15% pentafluoropropane; FIFLOW® BB61; Innovation Company, De Hue, France) or BTX (60-75% perfluorohexane, 15-20% perfluoroperhydrophenanthrene, 10-15% perfluorodecalin and 1-5% perfluorodimethylcyclohexane; FIFLOW® BTX; Innovation Company, De Hue, France) was added to the mixture and stirred for 30 minutes. The mixture was homogenized at 8100 rpm for 30 seconds in a high-speed homogenizer (HG-15A; Daehan Science, Wonju, Korea) to obtain a crude emulsion, and then treated in an LV1-30K microfluidics (Microfluidics, Westwood, Massachusetts, USA) at 15,000 psi (about 1034 bar) for 5 cycles. Next, oxygen was bubbled into the crude emulsion at a rate of 1 mL/min to prepare a nanoemulsion containing oxygen gas.

<Test Example 9> Evaluation of the Size and Polydispersity Index of Nanoemulsion 1. Material Preparation A nanoemulsion composition was prepared according to the composition of Table 5 below. The content of each ingredient was expressed as a relative content ratio, and the unit was weight %.

TABLE 5

| Category | PFOB | BB61 | BTX | Soy Phosphatidylcholine | Tween 80 | Water |
|---|---|---|---|---|---|---|
| Example 36 | 60 | — | — | 1.875 | 0.625 | to 100 |
| Comparative Example 1 | — | 60 | — | 1.875 | 0.625 | to 100 |
| Example 37 | — | — | 60 | 1.875 | 0.625 | to 100 |

2. Evaluation Method of the Size and Polydispersity Index of Nanoemulsion

The particle size, surface charge, and polydispersity index (PDI) of the prepared nanoemulsion were measured and evaluated using a zeta potential/particle size analyzer (ELSZ-2000 series, Otsuka Electronics, Japan). The measurement was performed by diluting the nanoemulsion sample for evaluation with phosphate buffered saline (PBS; Corning, USA) and then putting the diluted nanoemulsion sample into the analyzer. The result was shown in FIG. 10 (particle size unit: nm).

3. Evaluation Result of the Size and Polydispersity Index of Nanoemulsion

Figure 10:
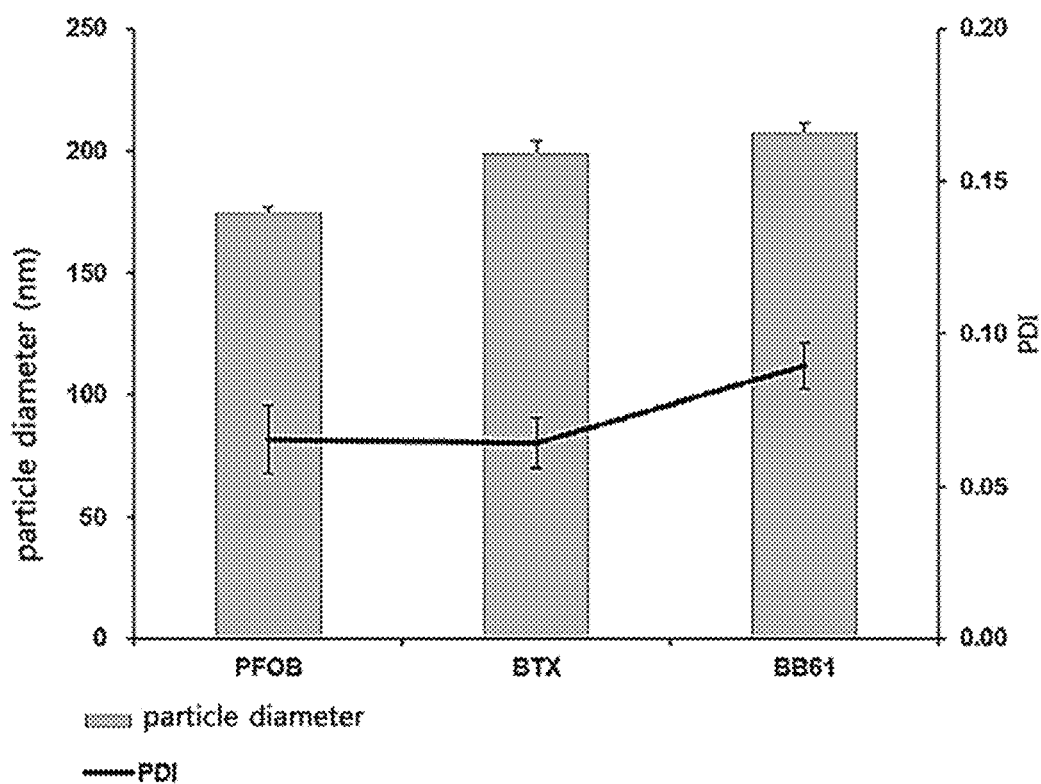
FIGS. 10 and 11 are graphs showing the evaluation results of the size and polydispersity index of nanoemulsion.

It was confirmed from FIG. 10 that the nanoemulsion of Comparative Example 1 had a large particle size and a polydisperse distribution. On the other hand, in the case of the nanoemulsion of Comparative Example 1, a lot of bubbles were formed during production, and in particular, the nanoemulsion of Comparative Example 1 produced bubbles to the extent that it was impossible to manufacture.

<Preparation Example 3> Preparation of Oxygen Sustained Release Nanoparticles

Water; oleyl polyoxyl-6 glyceride and propylene glycol monocaprylate (Gatefosse, Saint-Priest, France); soy phosphatidylcholine (Lipoid, Ludwigshafen, Germany), hydrogenated lecithin (Lipoid P100-3, Lipoid GmbH) or polyglyceryl-10 stearate (Nikkol decaglyn 1-sv, Nikko Chemicals Co., Ltd.); and Tween 80 (Merck, Darmstadt, Germany), inulin lauryl carbamate (Inutec SL1, Creachem), polyglyceryl-10 laurate (Sunsoft Q-12Y-C, Taiyo Chemical), glyceryl stearate Citrate (Dracorin CE, Symrise) or sodium stearoyl glutamate (Eumulgin SG, BASF) was dissolved in PBS (pH 7.4) and stirred at room temperature for 30 minutes using a magnetic stirrer.

PFOB (Sinquest Laboratories, FL, USA), perfluorodecalin (PFD, Sigma, St Louis, MO) and/or perfluorohexane (PFH, Sigma, St Louis, MO) was then added to the mixture and stirred for 30 minutes. The mixture was homogenized at 8100 rpm for 30 seconds in a high-speed homogenizer (HG-15A; Daehan Science, Wonju, Korea) to obtain a crude emulsion, and then treated in an LV1-30K microfluidics (Microfluidics, Westwood, Massachusetts, USA) at 15,000 psi (about 1034 bar) for 5 cycles. Next, oxygen was bubbled into the crude emulsion at a rate of 1 mL/min to prepare a nanoemulsion containing oxygen gas.

<Preparation Example 4> Preparation of a Nanoemulsion Composition

Nanoemulsion compositions were prepared according to the compositions of Tables 6 to 12 below. The content of each ingredient was expressed as a relative content ratio, and the unit was weight %.

TABLE 6

| Category | PFOB | PFD | PFH | Soy Phosphatidylcholine | Tween 80 | Water |
|---|---|---|---|---|---|---|
| Example 36 | 60 | — | — | 1.875 | 0.625 | to 100 |
| Example 38 | — | 60 | — | 1.875 | 0.625 | to 100 |
| Example 39 | — | 45 | 45 | 1.875 | 0.625 | to 100 |
| Example 40 | — | 30 | 30 | 1.875 | 0.625 | to 100 |
| Example 41 | — | 45 | 45 | 1.875 | 0.625 | to 100 |
| Example 42 | — | — | 60 | 1.875 | 0.625 | to 100 |

TABLE 7

| Category | PFD | PFH | Hydrogenated lecithin | Inulin lauryl carbamate | Water |
|---|---|---|---|---|---|
| Example 43 | 37.5 | 12.5 | 3.75 | 1.25 | to 100 |
| Example 44 | 37.5 | 12.5 | 3 | 1 | to 100 |
| Example 45 | 37.5 | 12.5 | 2.25 | 0.75 | to 100 |
| Example 46 | 37.5 | 12.5 | 1.5 | 0.5 | to 100 |
| Example 47 | 37.5 | 12.5 | 0.75 | 0.25 | to 100 |
| Example 48 | 37.5 | 12.5 | 4 | 1 | to 100 |
| Example 49 | 37.5 | 12.5 | 3.2 | 0.8 | to 100 |
| Example 50 | 37.5 | 12.5 | 2.4 | 0.6 | to 100 |
| Example 51 | 37.5 | 12.5 | 1.6 | 0.4 | to 100 |
| Example 52 | 37.5 | 12.5 | 0.8 | 0.2 | to 100 |

TABLE 8

| Category | PFD | PFH | Hydrogenated lecithin | Polyglyceryl-10 laurate | Water |
|---|---|---|---|---|---|
| Example 53 | 37.5 | 12.5 | 3.75 | 1.25 | to 100 |
| Example 54 | 37.5 | 12.5 | 3 | 1 | to 100 |
| Example 55 | 37.5 | 12.5 | 2.25 | 0.75 | to 100 |
| Example 56 | 37.5 | 12.5 | 1.5 | 0.5 | to 100 |
| Example 57 | 37.5 | 12.5 | 0.75 | 0.25 | to 100 |
| Example 58 | 37.5 | 12.5 | 4 | 1 | to 100 |
| Example 59 | 37.5 | 12.5 | 3.2 | 0.8 | to 100 |
| Example 60 | 37.5 | 12.5 | 2.4 | 0.6 | to 100 |
| Example 61 | 37.5 | 12.5 | 1.6 | 0.4 | to 100 |
| Example 62 | 37.5 | 12.5 | 0.8 | 0.2 | to 100 |

TABLE 9

| Category | PFD | PFH | Polyglyceryl-10 stearate | Glyceryl stearate citrate | Water |
|---|---|---|---|---|---|
| Example 63 | 37.5 | 12.5 | 4 | 1 | to 100 |
| Example 64 | 37.5 | 12.5 | 3.2 | 0.8 | to 100 |
| Example 65 | 37.5 | 12.5 | 2.4 | 0.6 | to 100 |
| Example 66 | 37.5 | 12.5 | 1.6 | 0.4 | to 100 |
| Example 67 | 37.5 | 12.5 | 0.8 | 0.2 | to 100 |

TABLE 10

| Category | PFD | PFH | Polyglyceryl-10 stearate | Inulin lauryl carbamate | Water |
|---|---|---|---|---|---|
| Example 68 | 37.5 | 12.5 | 4 | 1 | to 100 |
| Example 69 | 37.5 | 12.5 | 3.2 | 0.8 | to 100 |
| Example 70 | 37.5 | 12.5 | 2.4 | 0.6 | to 100 |
| Example 71 | 37.5 | 12.5 | 1.6 | 0.4 | to 100 |
| Example 72 | 37.5 | 12.5 | 0.8 | 0.2 | to 100 |

TABLE 11

| Category | PFD | PFH | Polyglyceryl-10 stearate | Sodium stearoyl glutamate | Water |
|---|---|---|---|---|---|
| Example 73 | 37.5 | 12.5 | 4 | 1 | to 100 |
| Example 74 | 37.5 | 12.5 | 3.2 | 0.8 | to 100 |
| Example 75 | 37.5 | 12.5 | 2.4 | 0.6 | to 100 |
| Example 76 | 37.5 | 12.5 | 1.6 | 0.4 | to 100 |
| Example 77 | 37.5 | 12.5 | 0.8 | 0.2 | to 100 |

TABLE 12

| Category | PFD | PFH | Hydrogenated lecithin | Cholesterol | Water |
|---|---|---|---|---|---|
| Example 78 | 37.5 | 12.5 | 3.75 | 1.25 | to 100 |
| Example 79 | 37.5 | 12.5 | 3 | 1 | to 100 |

TABLE 12-continued

| Category | PFD | PFH | Hydrogenated lecithin | Cholesterol | Water |
|---|---|---|---|---|---|
| Example 80 | 37.5 | 12.5 | 2.25 | 0.75 | to 100 |
| Example 81 | 37.5 | 12.5 | 1.5 | 0.5 | to 100 |
| Example 82 | 37.5 | 12.5 | 0.75 | 0.25 | to 100 |
| Example 83 | 37.5 | 12.5 | 4 | 1 | to 100 |
| Example 84 | 37.5 | 12.5 | 3.2 | 0.8 | to 100 |
| Example 85 | 37.5 | 12.5 | 2.4 | 0.6 | to 100 |
| Example 86 | 37.5 | 12.5 | 1.6 | 0.4 | to 100 |
| Example 87 | 37.5 | 12.5 | 0.8 | 0.2 | to 100 |

<Test Example 10> Evaluation of the Particle Size and Polydisperisty Index of Nanoemulsion 1. Material Preparation The nanoemulsion compositions of Example 22, Examples 24-28 were used.

Figure 11:
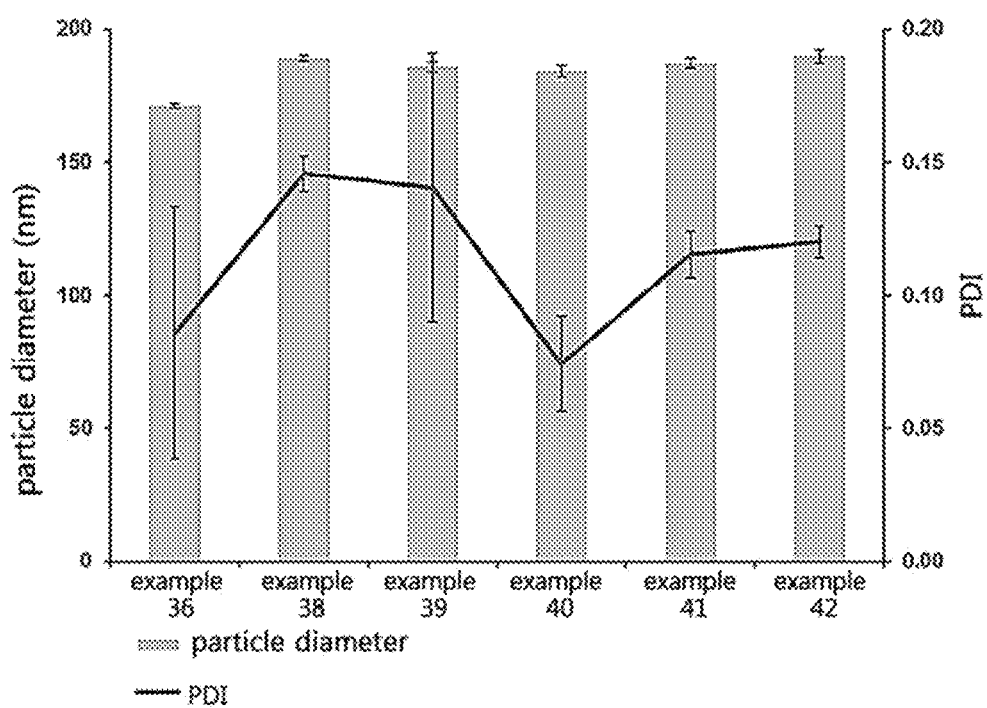

2. Evaluation Method of the Particle Size and Polydispersity Index of Nanoemulsion The particle size, surface charge, and polydispersity index (PDI) of the prepared nanoemulsion were measured using a zeta potential/particle size analyzer (ELSZ-2000 series, Otsuka Electronics, Japan). The measurement was performed by diluting the nanoemulsion sample for evaluation with phosphate buffered saline (PBS; Corning, USA) and then putting the diluted nanoemulsion sample into the analyzer. The result was shown in FIG. 11 (particle size unit: nm).

3. Evaluation Result of the Particle Size and Polydispersity Index of Nanoemulsion It was confirmed from FIG. 11 that all the nanoemulsions of Examples 36 and 38 to 42 had excellent properties with the particle size of 200 nm or less.

<Test Example 11> Size Evaluation of Nanoemulsion According to Temperature and Time 1. Material Preparation The nanoemulsion compositions of Examples 36 and 38 to 42 were used.

2. Evaluation Method of the Size Particle of Nanoemulsion

The same method as the evaluation method in Test Example 10 was performed. The measurement result at a temperature of 4° C. was shown in FIG. 12a, and the measurement result at a temperature of 37° C. was shown in FIG. 12b (particle size unit: nm).

3. Evaluation Result of the Particle Size of Nanoemulsion

Figure 12A:
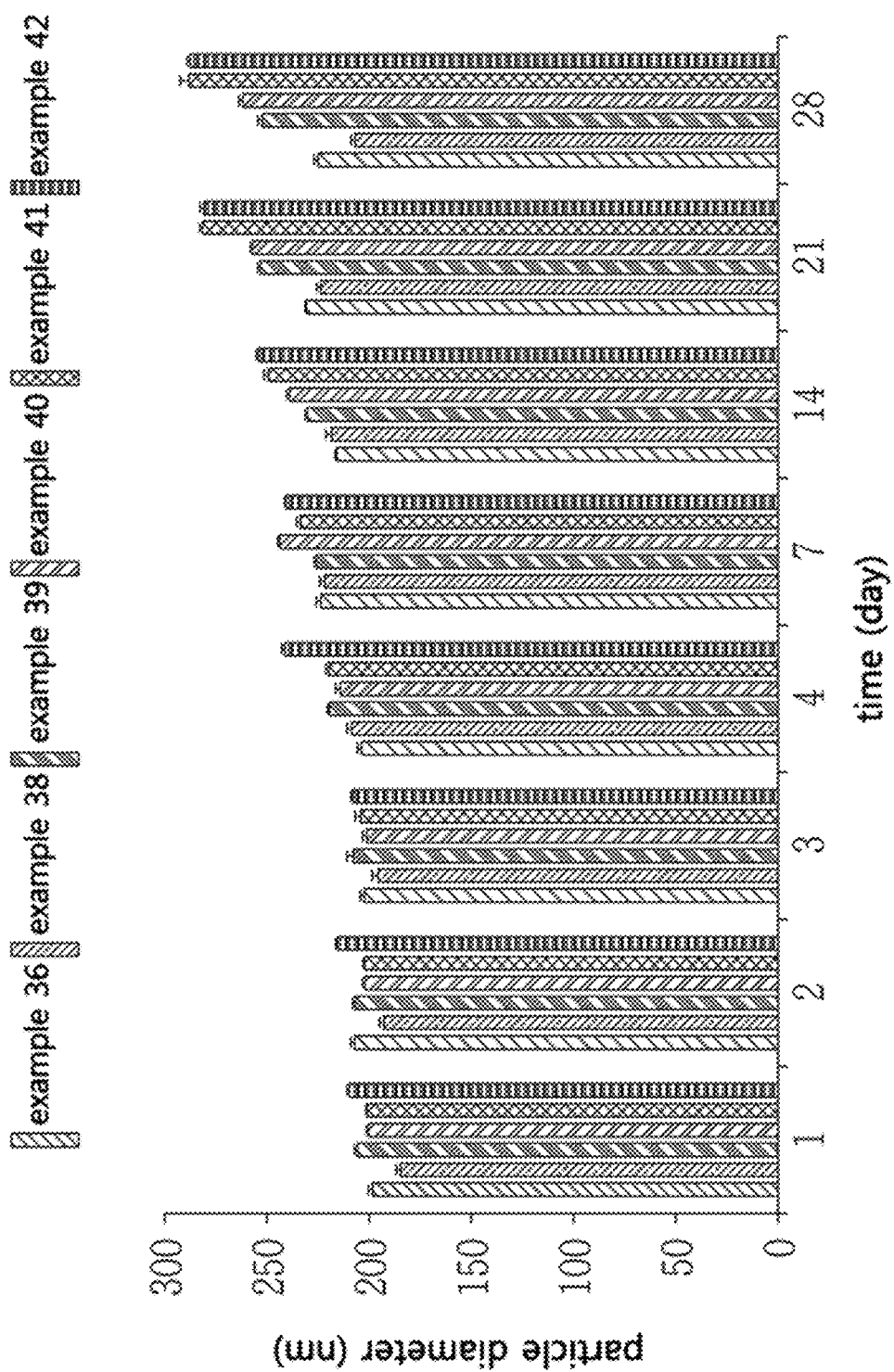
FIG. 12a and FIG. 12b are graphs showing the evaluation results of the size of nanoemulsion according to temperature and time.
Figure 12B:
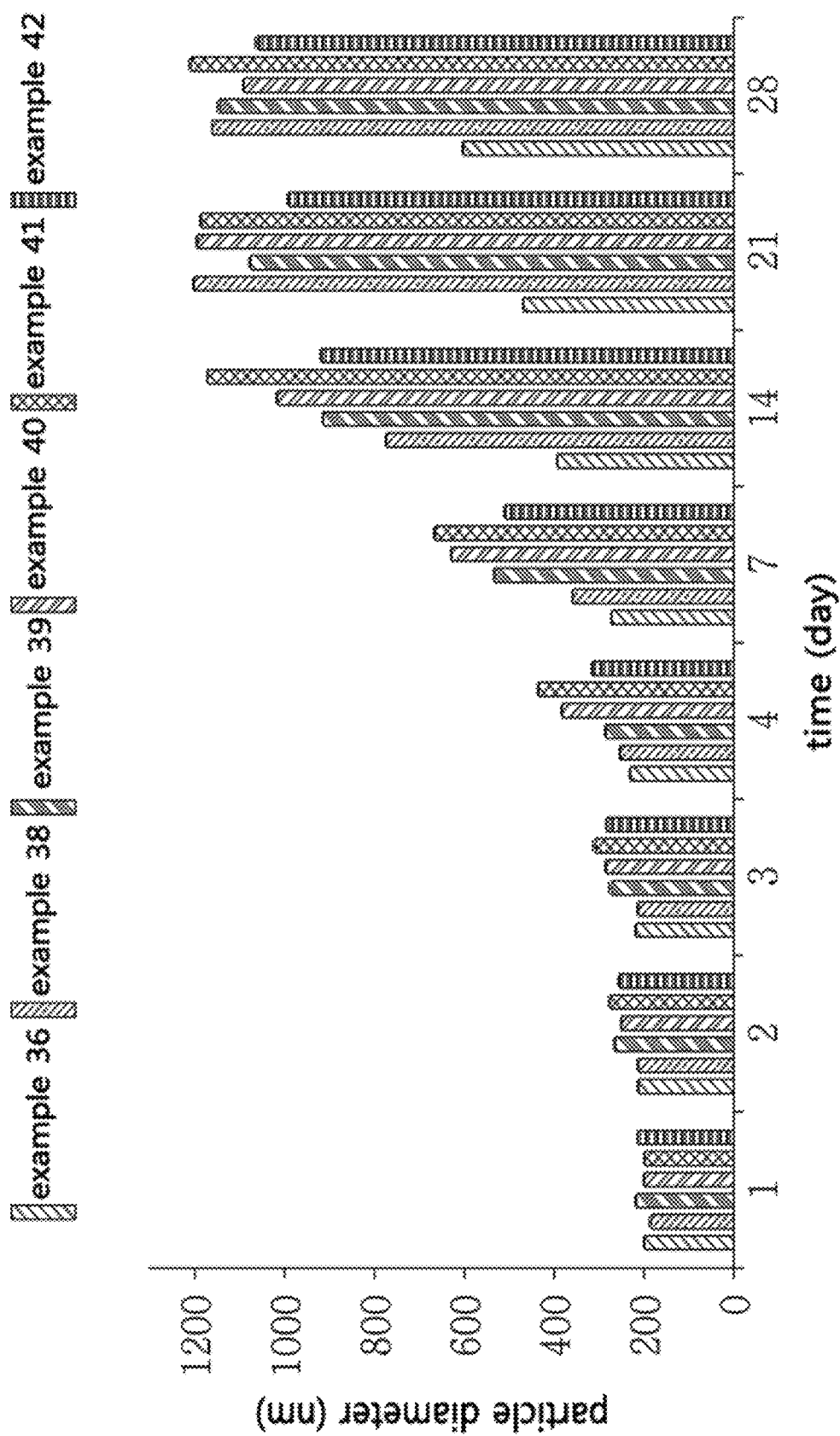

When stored at 4° C., the particle size of the nanoemulsion increased with time as shown in FIG. 12a, and this trend was slightly different depending on the concentration of PFH. More specifically, as the concentration of PFH increased, the particle size of the nanoemulsion further increased. In particular, in the case of the nanoemulsion of Example 38 without PFH, there was no significant change in particle size for 28 days, and in the case of the nanoemulsion of Example 42 without PFD, the particle size increased by about 40% for 28 days. Therefore, it can be expected that PFH affects the particle stability of the nanoemulsion. As shown in FIG. 12b, when stored at 37° C., the nanoemulsion showed a tendency to increase in particle size by about 200 to 530% compared to the initial size in all groups after 28 days.

<Test Example 12> Evaluation of the Oxygen Encapsulation Rate of a Nanoemulsion Composition 1. Material Preparation The nanoemulsion compositions of Examples 36 and 38 to 42 were used.

2. Evaluation Method of the Oxygen Encapsulation Rate of a Nanoemulsion Composition The oxygen concentration in the nanoemulsion was evaluated using a Fospor-R oxygen sensor (Ocean Optics, USA). A Fospor-R oxygen sensor probe was placed in a container containing the nanoemulsion solution to measure the oxygen concentration in real time. The result was shown in FIG. 13 (unit: ppm (v/w)).

3. Evaluation Result of the Oxygen Encapsulation Rate of Nanoemulsion

Figure 13:
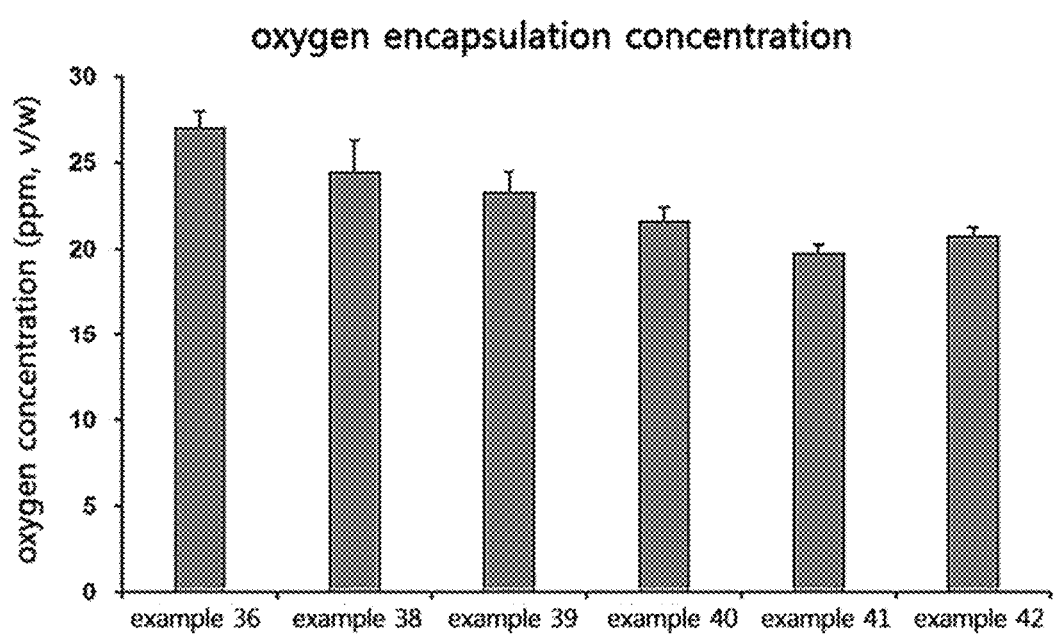
FIG. 13 is a graph showing the evaluation result of the oxygen encapsulation rate of a nanoemulsion composition.

It was confirmed from FIG. 13 that 20 ppm (v/w) or more of oxygen was encapsulated in all of the nanoemulsions of Examples 36 and 38 to 42. More specifically, the PFOB nanoemulsion of Example 36 contained about 27 ppm, and the PFD/PFH nanoemulsions of Examples 38 to 42 contained 20 to 25 ppm of oxygen depending on the mixing ratio. Through this, it can be seen that the oxygen encapsulation concentration decreases as the concentration of PFH increases in the PFD/PFH nanoemulsions of Examples 38 to 42.

<Test Example 13> Evaluation of the Oxygen Encapsulation Rate of a Nanoemulsion Composition Over Time 1. Material Preparation The nanoemulsion compositions of Examples 36 and 38 to 42 were used.

2. Evaluation Method of the Oxygen Encapsulation Rate of a Nanoemulsion Composition The oxygen concentration in the nanoemulsion was evaluated using a Fospor-R oxygen sensor (Ocean Optics, USA). A Fospor-R oxygen sensor probe was placed in a container containing the nanoemulsion solution to measure the oxygen concentration in real time. The result was shown in FIG. 14a (unit: ppm (v/w)). The result of normalization based on the initial concentration was shown in FIG. 14b.

Figure 14A:
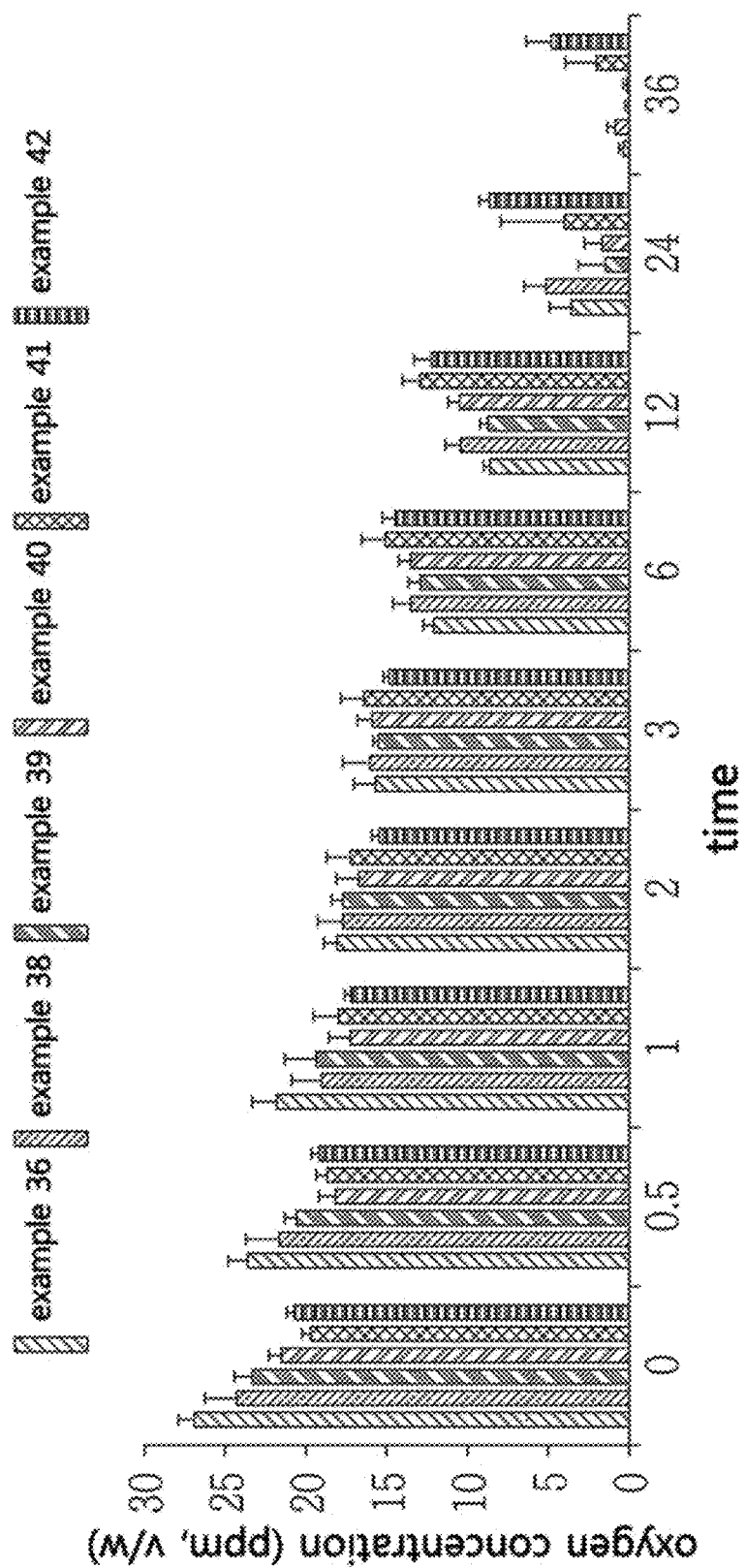
FIG. 14a and FIG. 14b are graphs showing the evaluation result of the oxygen encapsulation rate of a nanoemulsion composition according to time.
Figure 14B:
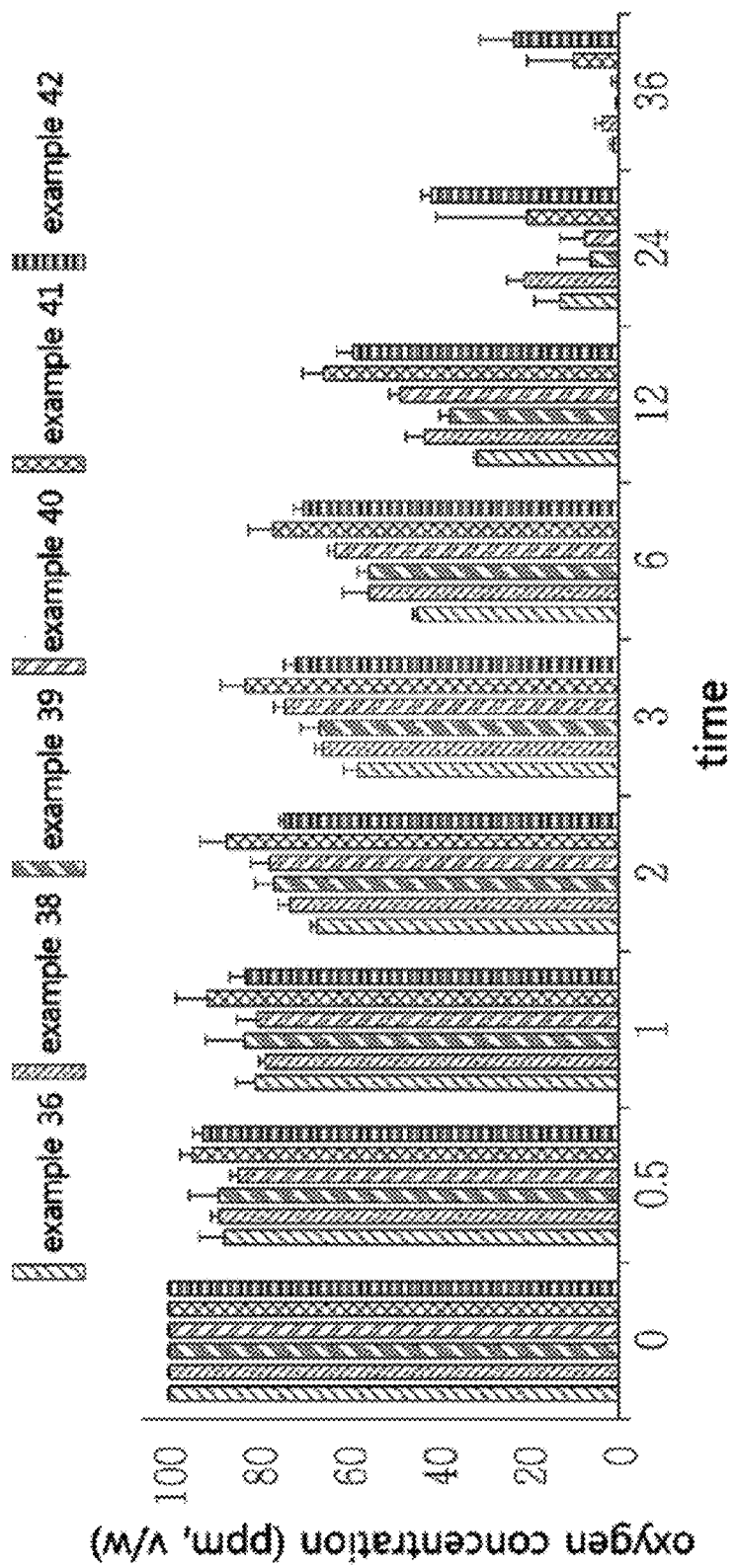

3. Evaluation Result of the Oxygen Encapsulation Rate of a Nanoemulsion Composition As shown in FIGS. 14a and 14b, the oxygen concentration remaining in the PFOB nanoemulsion of Example 36 was high until 1 hour after the start of the evaluation, but after that, the oxygen concentration remaining in the PFD/PFH nanoemulsions of Examples 38 to 42 was high with lapse of time. In particular, the higher the concentration of PFH, the higher the concentration of residual oxygen, and from this, it can be seen that the release of oxygen into the atmosphere is controlled by PFH.

<Test Example 14> Evaluation of the Particle Size and Polydispersity Index of a Nanoemulsion Composition According to the Content of Main Surfactant and Auxiliary Surfactant 1. Material Preparation The nanoemulsion compositions of Examples 43 to 52 were used.

Figure 15:
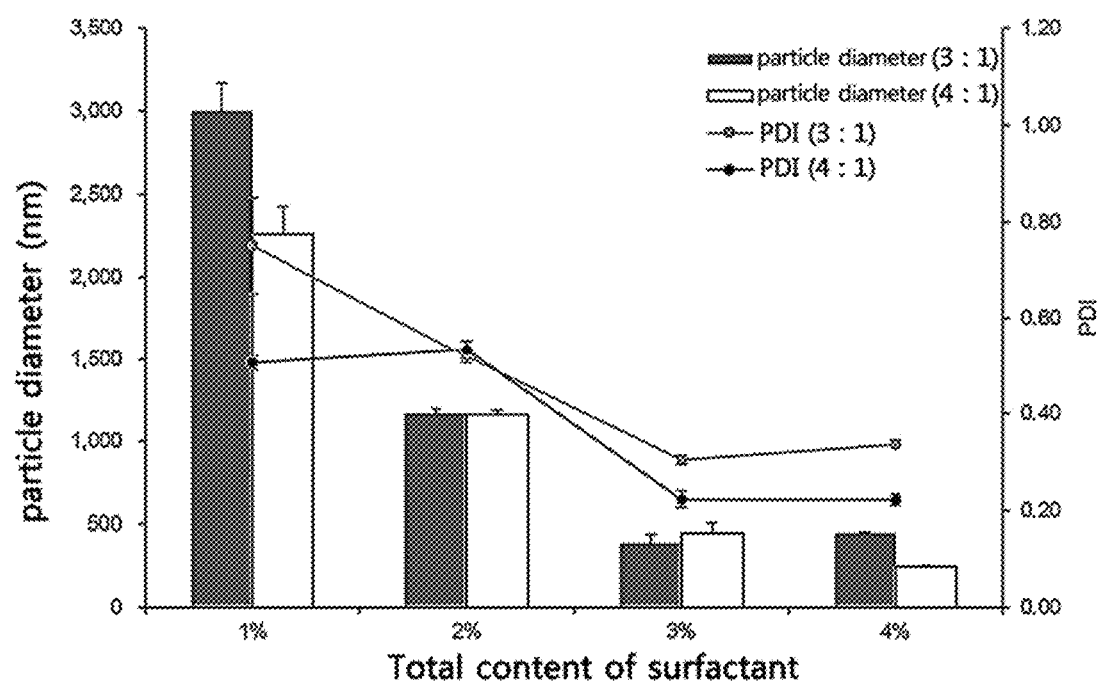
FIGS. 15 and 16 are graphs showing the evaluation results of the particle size and polydispersity index of a nanoemulsion composition according to the content of a main surfactant and an auxiliary surfactant.

2. Evaluation Method of the Particle Size and Polydispersity Index of a Nanoemulsion Composition The same method as the evaluation method in Test Example 10 was performed. The result was shown in FIG. 15 (particle size unit: nm).

3. Evaluation Result of the Particle Size and Polydispersity Index of a Nanoemulsion Composition It was confirmed from FIG. 15 that the size of the particles increased as the total content of the surfactant increased. However, as the total content of the surfactant increased, the viscosity and foaming degree of the nanoemulsion showed a tendency to increase proportionally.

<Test Example 15> Evaluation of the Particle Size and Polydispersity Index of a Nanoemulsion Composition According to the Content of Main Surfactant and Auxiliary Surfactant 1. Material Preparation The nanoemulsion compositions of Examples 53 to 62 were used.

2. Evaluation Method of the Particle Size and Polydispersity Index of a Nanoemulsion Composition The same method as the evaluation method in Test Example 10 was performed. The result was shown in FIG. 16 (particle size unit: nm).

Figure 16:
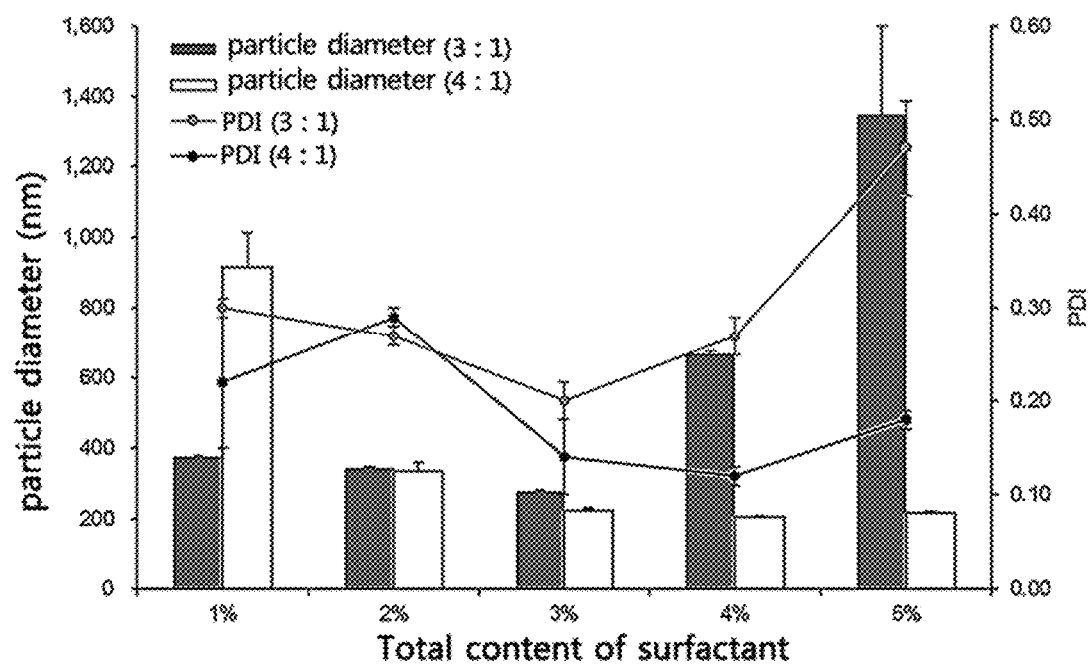

3. Evaluation Result of the Particle Size and Polydispersity Index of a Nanoemulsion Composition As shown in FIG. 16, in the case of Examples 53 to 57 in which the content ratio of the main surfactant and the auxiliary surfactant was 3:1, it was found that the particle size increased as the total content of the surfactant increased. However, in the case of Examples 58 to 62 in which the content ratio of the main surfactant and the auxiliary surfactant was 4:1, it was found that the particle size decreased as the total content of the surfactant increased. In particular, Example 59 formed the smallest particle size (203.99 nm).

<Test Example 16> Evaluation of the Particle Size and Polydispersity Index of a Nanoemulsion Composition According to Temperature and Time 1. Material Preparation The nanoemulsion compositions of Examples 58 to 62 were used.

2. Evaluation Method of the Size and Polydispersity Index of a Nanoemulsions

Figure 17:
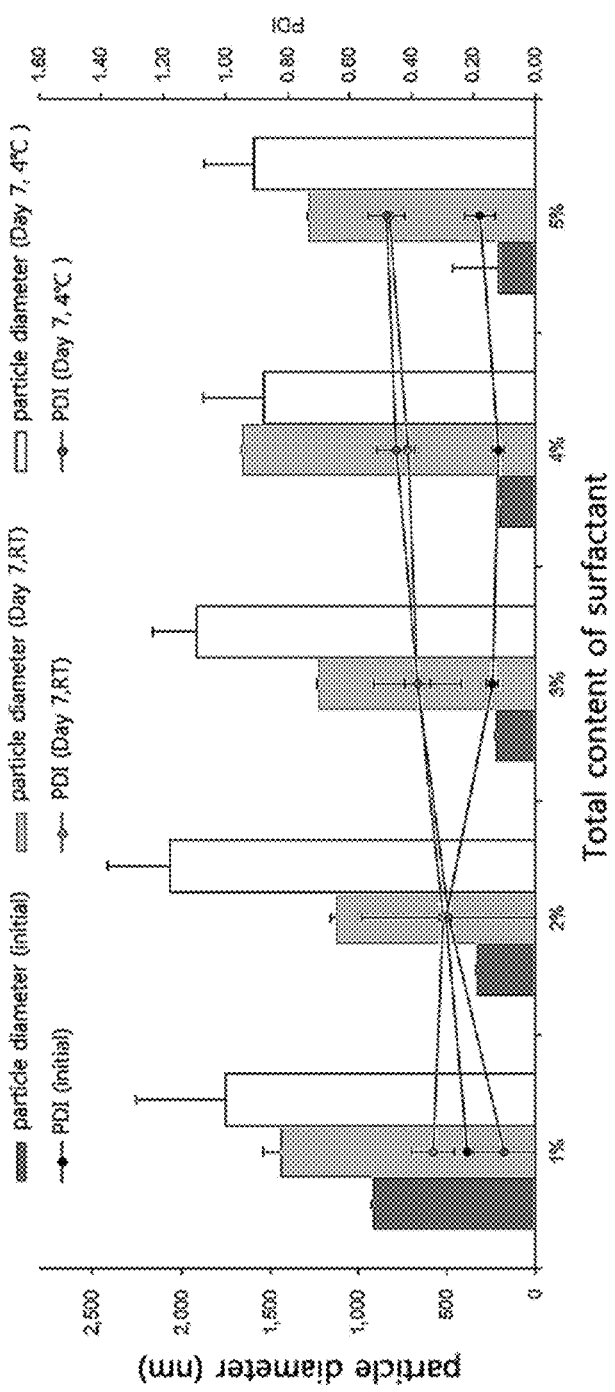
FIG. 17 is a graph showing the evaluation result of the particle size and polydispersity index of a nanoemulsion composition according to temperature and time.

The same method as the evaluation method in Test Example 10 was performed. The results respectively measured at a temperature of 4° C. and at room temperature (RT) were shown in FIG. 17 (particle size unit: nm).

3. Evaluation Result of the Particle Size and Polydispersity Index of a Nanoemulsion Composition It was confirmed from FIG. 17 that the nanoemulsion particle size increased at both 4° C. and room temperature (RT) when 7 days had elapsed. In addition, it was found that the degree of particle size increase was different according to the storage temperature condition, and the refrigerated storage condition promoted the particle size increase.

<Test Example 17> Evaluation of the Particle Size and Polydispersity Index of a Nanoemulsion Composition According to the Content of Main Surfactant and Auxiliary Surfactant 1. Material Preparation The nanoemulsion compositions of Examples 63 to 67 were used.

Figure 18:
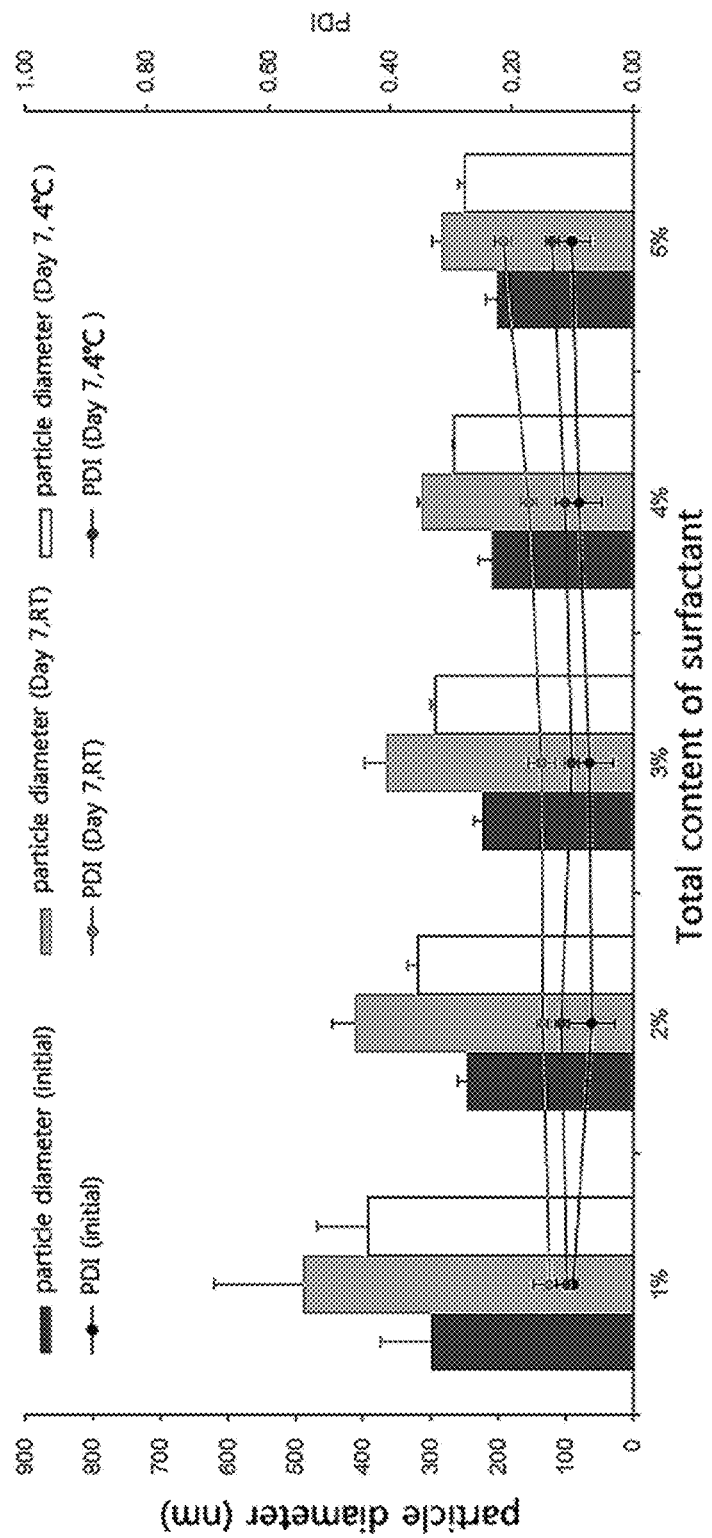
FIGS. 18 to 20 are graphs showing the evaluation results of the particle size and polydispersity index of a nanoemulsion composition according to the content of a main surfactant and an auxiliary surfactant.

2. Evaluation Method of the Particle Size and Polydispersity Index of a Nanoemulsion Composition The same method as the evaluation method in Test Example 10 was performed. The results respectively measured at 4° C. and room temperature (RT) were shown in FIG. 18 (particle size unit: nm).

3. Evaluation Result of the Particle Size and Polydispersity Index of a Nanoemulsion Composition It was confirmed from FIG. 18 that all the nanoemulsion compositions immediately after preparation were formed with a particle size of less than 300 nm. In particular, Example 63 formed the smallest particle size (203.99 nm). In addition, it was found that the nanoemulsion particle size increased at both 4° C. and room temperature (RT) when 7 days had elapsed. Compared to the case of room temperature (RT), the increase in particle size was relatively suppressed at a temperature of 4° C. Examples 63 and 64 showed good increase in particle size after 7 days.

<Test Example 18> Evaluation of the Particle Size and Polydispersity Index of a Nanoemulsion Composition According to the Content of Main Surfactant and Auxiliary Surfactant 1. Material Preparation The nanoemulsion compositions of Examples 68 to 72 were used.

Figure 19:
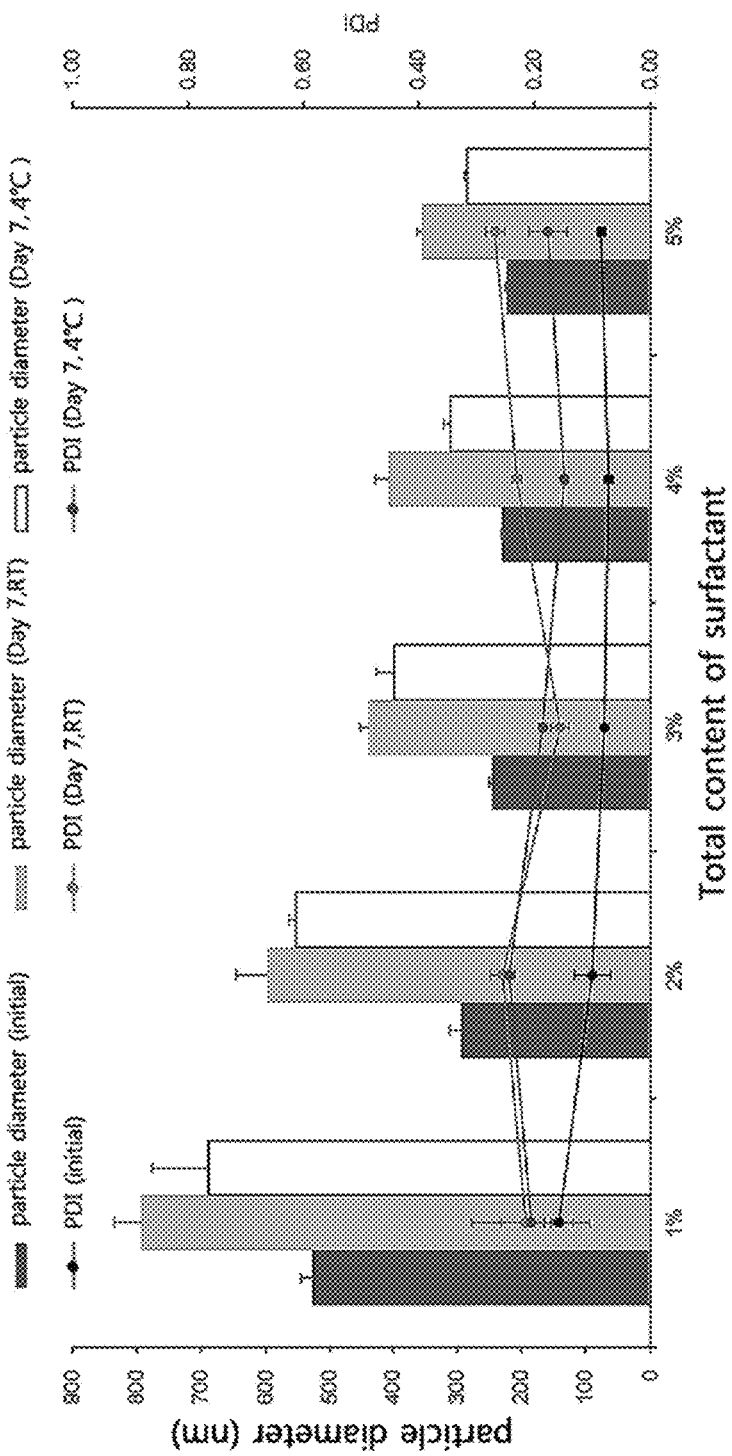

2. Evaluation Method of the Particle Size and Polydispersity Index of a Nanoemulsion Composition The same method as the evaluation method in Test Example 10 was performed. The results respectively measured at a temperature of 4° C. and at room temperature (RT) were shown in FIG. 19 (particle size unit: nm).

3. Evaluation Result of the Particle Size and Polydispersity Index of a Nanoemulsion Composition It was confirmed from FIG. 19 that the size of the particles decreased as the total content of the surfactant increased both at a temperature of 4° C. and at room temperature (RT). In particular, Example 68 formed the smallest particle size (220 nm). The viscosity was not high enough to affect the preparation and the degree of foam formation was also weak. It could be seen that the particle size of the nanoemulsion increased at a time point of 7 days in both the temperature of 4° C. and the room temperature (RT). Compared to the case of room temperature (RT), the increase in particle size was relatively suppressed at a temperature of 4° C.

<Test Example 19> Evaluation of the Particle Size and Polydispersity Index of a Nanoemulsion Composition According to the Content of Main Surfactant and Auxiliary Surfactant 1. Material Preparation The nanoemulsion compositions of Examples 73 to 77 were used.

Figure 20:
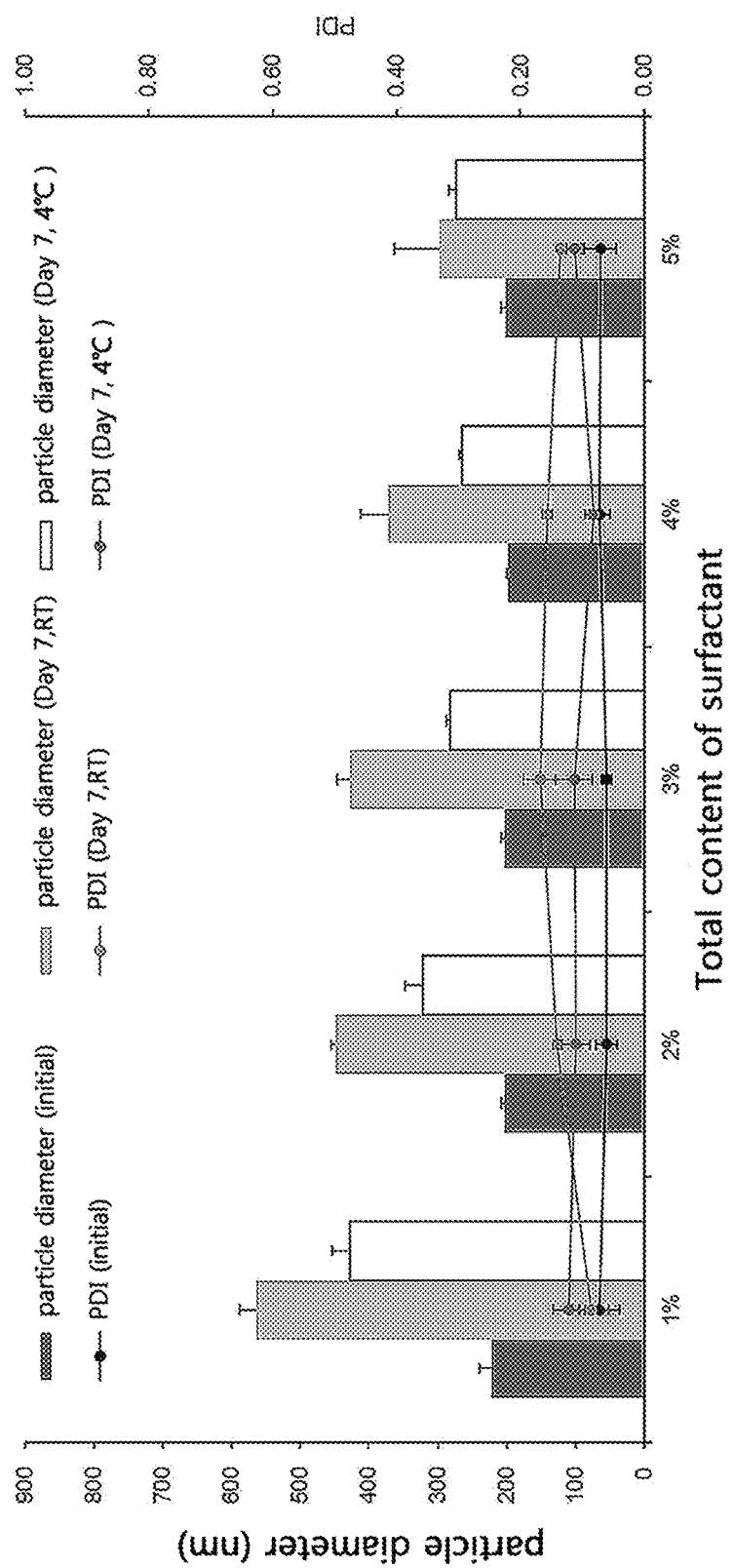

2. Evaluation Method of the Particle Size and Polydispersity Index of a Nanoemulsion Composition The same method as the evaluation method in Test Example 10 was performed. The results respectively measured at a temperature of 4° C. and at room temperature (RT) were shown in FIG. 20 (particle size unit: nm).

3. Evaluation Result of the Particle Size and Polydispersity Index of a Nanoemulsion Composition It was confirmed from FIG. 20 that all nanoemulsion compositions immediately after preparation were not significantly affected by the total content of surfactant and formed similar particle sizes. When stored at a temperature of 4° C., it could be seen that the total content of the surfactant affected the stability of the nanoemulsion at the time of 7 days. For both the temperature of 4° C. and the room temperature (RT), the tendency of the particle size increase of the formulation decreased as the total content of the surfactant increased.

<Test Example 20> Evaluation of the Oxygen Encapsulation Rate of a Nanoemulsion Composition 1. Material Preparation The nanoemulsion compositions of Examples 63, 68 and 73 were used. Also, a composition containing PFOB, polyglyceryl-10 stearate as the main surfactant, and glyceryl stearate citrate, inulin lauryl carbamate, sodium stearoyl glutamate as the auxiliary surfactants was used.

2. Evaluation Method of the Oxygen Encapsulation Rate of a Nanoemulsion Composition The same method as the evaluation method in Test Example 3 was performed. The oxygen concentration of each formulation was measured before oxygen purging, and the oxygen concentration of each formulation after oxygen purging was measured. The result was shown in FIG. 21 (unit: ppm (v/w)).

3. Evaluation Result of the Oxygen Encapsulation Rate of a Nanoemulsion

Figure 21:
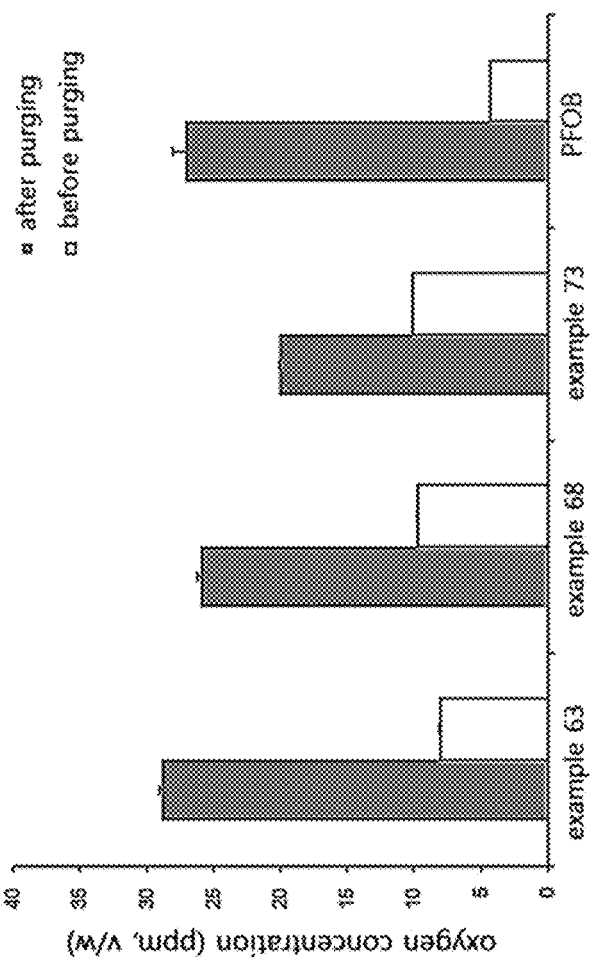
FIG. 21 is a graph showing the evaluation result of an oxygen encapsulation rate of a nanoemulsion composition.

It was confirmed from FIG. 21 that oxygen of 20 ppm (v/w) or more was encapsulated in all of the nanoemulsions of Examples 63, 68 and 73. After oxygen purge, the formulation of Example 63 had an oxygen encapsulation concentration of 28.9 ppm (v/w), which was higher than that of the composition containing PFOB having an oxygen concentration of 27.1 ppm (v/w).

<Test Example 21> Evaluation of the Oxygen Release Rate of a Nanoemulsion Composition 1. Material Preparation The nanoemulsion compositions of Examples 63, 68 and 73 were used. Also, a composition containing PFOB, polyglyceryl-10 stearate as the main surfactant, and glyceryl stearate citrate, inulin lauryl carbamate, sodium stearoyl glutamate as the auxiliary surfactants was used.

2. Evaluation Method of the Oxygen Release Rate of a Nanoemulsion Composition

The same method as the evaluation method in Test Example 3 was performed. The oxygen concentration of each formulation was measured before oxygen purging, and the oxygen concentration of each formulation after oxygen purging was measured. The result was shown in FIG. 22a (unit: ppm (v/w)). The result of normalization based on the initial concentration was shown in FIG. 22b.

3. Evaluation Result of the Oxygen Release Rate of a Nanoemulsion Composition

Figure 22:
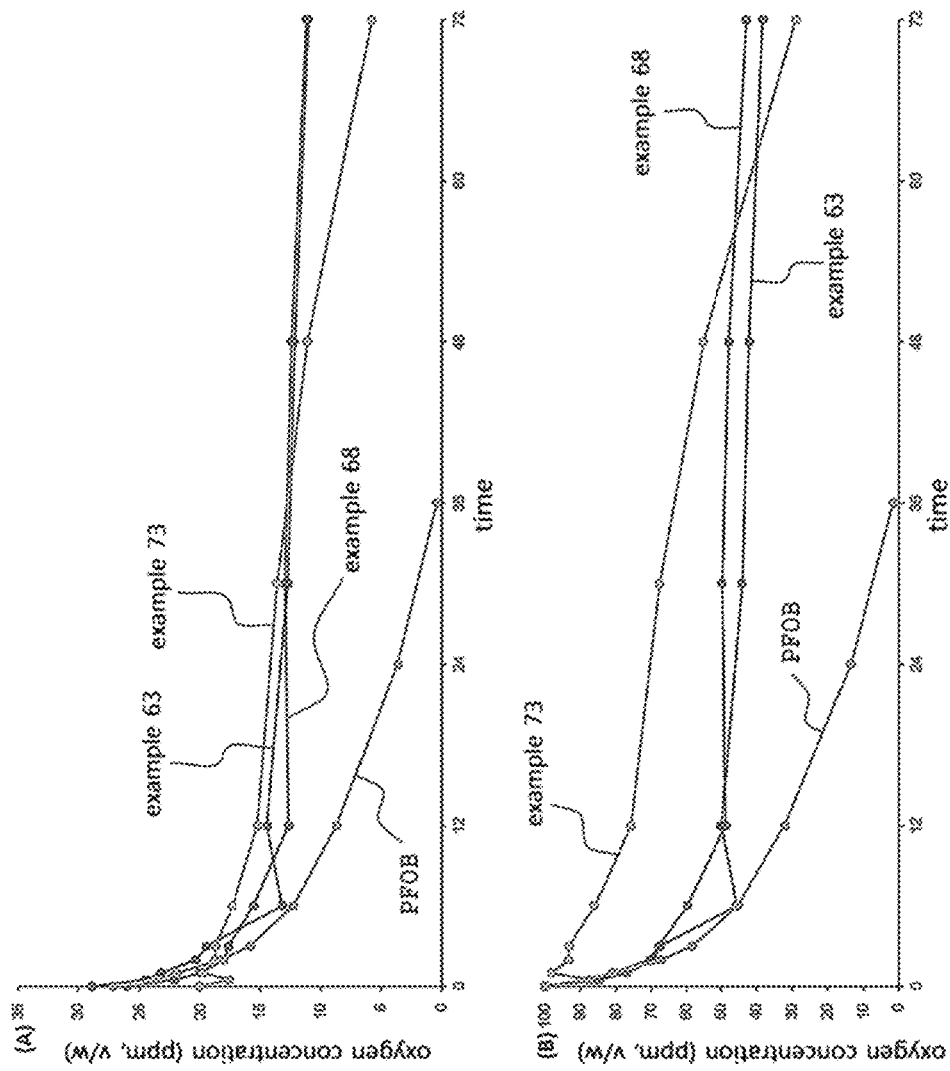
FIG. 22 is a graph showing the evaluation result of an oxygen release degree of a nanoemulsion composition.

As shown in FIG. 22a, the composition containing PFOB released all oxygen within 36 hours, but all of the nanoemulsions of Examples 63, 68, and 73 continued to release oxygen until 72 hours had elapsed, and contained the oxygen of 5 to 11 ppm (v/w). It could be seen from FIG. 22b that the oxygen concentration of 30 to 42% compared to the initial encapsulation amount was maintained for up to 72 hours.

Formulation examples of the composition according to one aspect of the present invention will be described below, but other various formulations are also applicable, which is not intended to limit the present invention, but merely to describe it in detail.

[Formulation Example 1] Shampoo

A shampoo was prepared in a commonly used method according to the composition shown in Table 13 below.

TABLE 13

| Ingredients | Content (wt %) |
| --- | --- |
| Perfluorooctyl bromide (PFOB) | 10.0 |
| Soy phosphatidylcholine | 2.5 |
| Tween 80 | 2.5 |
| Ammonium laureth sulfate | 10.0 |
| Glycol distearate | 2.0 |
| Cetyl alcohol | 0.6 |
| Cocamide MEA | 0.5 |
| Ammonium lauryl sulfate | 6.0 |
| Guar hydroxypropyltrimonium chloride | 0.15 |
| Polyquaternium-10 | 0.1 |
| Silicon | 0.5 |
| Distearyldimethylammonium chloride | 0.2 |
| Sodium cocoamphoacetate | 4.0 |
| Fragrance | 1.0 |
| Antiseptic | 0.03 |
| Citric acid | Adequate |
| Purified water | Balance |

[Formulation Example 2] Rinse

A rinse was prepared in a commonly used method according to the composition shown in Table 14 below.

TABLE 14

| Ingredients | Content (wt %) |
| --- | --- |
| Perfluorooctyl bromide (PFOB) | 10.0 |
| Soy phosphatidylcholine | 2.5 |
| Tween 80 | 2.5 |
| Cetyl alcohol | 3.0 |
| Glycerin monostearate | 1.0 |
| Hydroxyethyl cellulose | 1.0 |
| Propylene glycol | 4.0 |
| Methylparahydroxybenzoate | 0.2 |
| Stearyldimethylbenzylammonium chloride 25% | 10.0 |
| Fragrance | Adequate |
| Colorant | Adequate |
| Citric acid | Adequate |
| Purified water | Balance |

[Formulation Example 3] Ointment

An ointment was prepared in a commonly used method according to the composition shown in Table 15 below.

TABLE 15

| Ingredients | Content (wt %) |
| --- | --- |
| Perfluorooctyl bromide (PFOB) | 10.0 |
| Soy phosphatidylcholine | 2.5 |
| Tween 80 | 2.5 |
| Butylene glycol | 4.0 |
| Liquid paraffin | 15.0 |
| Beta glucan | 7.0 |
| Carbomer | 0.1 |
| Caprylic/Capric triglycerides | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Glycerin | 8.0 |
| Antiseptic, Colorant, Fragrance | Adequate |
| Purified water | Balance |

[Formulation Example 4] Massage Cream

A massage cream was prepared in a commonly used method according to the composition shown in Table 16 below.

TABLE 16

| Ingredients | Content (wt %) |
| --- | --- |
| Perfluorooctyl bromide (PFOB) | 10.0 |
| Soy phosphatidylcholine | 2.5 |
| Tween 80 | 2.5 |
| Glycerin | 8.0 |
| Butylene glycol | 4.0 |
| Liquid paraffin | 45.0 |
| Beta glucan | 7.0 |
| Carbomer | 0.1 |
| Caprylic/Capric triglyceride | 3.0 |
| Beeswax | 4.0 |
| Cetearyl glucoside | 1.5 |
| Sesquioleic acid sorbitan | 0.9 |
| Vaseline | 3.0 |
| Paraffin | 1.5 |
| Antiseptic, Colorant, Fragrance | Adequate |
| Purified water | Balance |

[Formulation Example 5] Hair Pack

A hair pack was prepared in a commonly used method according to the composition shown in Table 17 below.

TABLE 17

| Ingredients | Content (wt %) |
| --- | --- |
| Perfluorooctyl bromide (PFOB) | 10.0 |
| Soy phosphatidylcholine | 2.5 |
| Tween 80 | 2.5 |
| Glycerin | 4.0 |
| Polyvinyl alcohol | 15.0 |
| Hyaluronic acid extract | 5.0 |
| Beta glucan | 7.0 |

TABLE 17-continued

| Ingredients | Content (wt %) |
| --- | --- |
| Allantoin | 0.1 |
| Nonyl phenyl ether | 0.4 |
| Polysorbate 60 | 1.2 |
| Ethanol preservative | 6.0 |
| Antiseptic, Colorant, Fragrance | Adequate |
| Purified water | Balance |

[Formulation Example 6] Soft Capsule 9 mg of vitamin E, 9 mg of vitamin C, 2 mg of palm oil, 8 mg of hydrogenated vegetable oil, 4 mg of yellow wax and 9 mg of lecithin were mixed to the nanoemulsion composition of Example 2, and mixed according to a commonly used method to prepare a soft capsule filling solution. Soft capsules were prepared by filling 400 mg of the solution per capsule. In addition, a soft capsule sheet was prepared in a ratio of 66 parts by weight of gelatin, 24 parts by weight of glycerin, and 10 parts by weight of sorbitol solution, separately from the above, and the filling solution was filled to prepare a soft capsule containing 400 mg of the composition.

[Formulation Example 7] Tablet 9 mg of vitamin E, 9 mg of vitamin C, 200 mg of galactooligosaccharide, 60 mg of lactose, and 140 mg of maltose were mixed to the nanoemulsion composition of Example 2, granulated using a fluidized bed dryer, and 6 mg of sugar ester was added thereto. 500 mg of these compositions were compressed in a commonly used method to prepare tablets.

[Formulation Example 8] Injection

Injection was prepared in a commonly used method according to the composition shown in Table 18 below.

TABLE 18

| Ingredients | Content (mg) |
| --- | --- |
| Nanoemulsion composition of Example 2 | 10.0 |
| Sterile distilled water for injection | Adequate |
| pH controller | Adequate |

[Formulation Example 9] Health Drink

A health drink was prepared in a commonly used method according to the composition shown in Table 19 below.

TABLE 19

| Ingredients | Content (mg) |
| --- | --- |
| Nanoemulsion composition of Example 2 | 100 |
| Citric acid/oligosaccharide/taurine | Adequate |

[Formulation Example 10] Shampoo

A shampoo was prepared in a commonly used method according to the composition shown in Table 20 below.

TABLE 20

| Ingredients | Content (wt %) |
|---|---|
| Perfluorodecalin (PFD) | 37.5 |
| Perfluorohexane (PFH) | 12.5 |
| Polyglyceryl-10 stearate | 4 |
| Inulin lauryl carbamate | 1 |
| Ammonium laureth sulfate | 10.0 |
| Glycol distearate | 2.0 |
| Cetyl alcohol | 0.6 |
| Cocamide MEA | 0.5 |
| Ammonium lauryl sulfate | 6.0 |
| Guar hydroxypropyltrimonium chloride | 0.15 |
| Polyquaternium-10 | 0.1 |
| Silicon | 0.5 |
| Distearyldimethylammonium chloride | 0.2 |
| Sodium cocoamphoacetate | 4.0 |
| Fragrance | 1.0 |
| Antiseptic | 0.03 |
| Citric acid | Adequate |
| Purified water | Balance |

[Formulation Example 11] Rinse

A rinse was prepared in a commonly used method according to the composition shown in Table 21 below.

TABLE 21

| Ingredients | Content (wt %) |
|---|---|
| Perfluorodecalin (PFD) | 37.5 |
| Perfluorohexane (PFH) | 12.5 |
| Polyglyceryl-10 Stearate | 4 |
| Inulin lauryl carbamate | 1 |
| Cetyl alcohol | 3.0 |
| Glycerin monostearate | 1.0 |
| Hydroxyethyl cellulose | 1.0 |
| Propylene glycol | 4.0 |
| Methylparahydroxybenzoate | 0.2 |
| Stearyldimethylbenzylammonium chloride 25% | 10.0 |
| Fragrance | Adequate |
| Colorant | Adequate |
| Citric acid | Adequate |
| Purified water | Balance |

[Formulation Example 12] Ointment

An ointment was prepared in a commonly used method according to the composition shown in Table 22 below.

TABLE 22

| Ingredients | Content (wt %) |
|---|---|
| Perfluorodecalin (PFD) | 37.5 |
| Perfluorohexane (PFH) | 12.5 |
| Polyglyceryl-10 Stearate | 4 |
| Inulin lauryl carbamate | 4 |
| Butylene glycol | 4.0 |
| Liquid paraffin | 15.0 |
| Beta glucan | 7.0 |
| Carbomer | 0.1 |
| Caprylic/Capric triglycerides | 3.0 |
| Squalane | 1.0 |
| Cetearyl glucoside | 1.5 |
| Sorbitan stearate | 0.4 |
| Cetearyl alcohol | 1.0 |

TABLE 22-continued

| Ingredients | Content (wt %) |
|---|---|
| Beeswax | 4.0 |
| Glycerin | 8.0 |
| Antiseptic, Colorant, Fragrance | Adequate |
| Purified water | Balance |

[Formulation Example 13] Massage Cream

A massage cream was prepared in a commonly used method according to the composition shown in Table 23 below.

TABLE 23

| Ingredients | Content (wt %) |
|---|---|
| Perfluorodecalin (PFD) | 37.5 |
| Perfluorohexane (PFH) | 12.5 |
| Polyglyceryl-10 Stearate | 4 |
| Inulin lauryl carbamate | 1 |
| Glycerin | 8.0 |
| Butylene glycol | 4.0 |
| Liquid paraffin | 45.0 |
| Beta glucan | 7.0 |
| Carbomer | 0.1 |
| Caprylic/Capric triglycerides | 3.0 |
| Beeswax | 4.0 |
| Cetearyl glucoside | 1.5 |
| Sesquioleic acid sorbitan | 0.9 |
| Vaseline | 3.0 |
| Paraffin | 1.5 |
| Antiseptic, Colorant, Fragrance | Adequate |
| Purified water | Balance |

[Formulation Example 14] Hair Pack

A hair pack was prepared in a commonly used method according to the composition shown in Table 24 below.

TABLE 24

| Ingredients | Content (wt %) |
|---|---|
| Perfluorodecalin (PFD) | 37.5 |
| Perfluorohexane (PFH) | 12.5 |
| Poly glyceryl-10 Stearate | 4 |
| Inulin lauryl cabamate | 1 |
| Glycerin | 4.0 |
| Polyvinyl alcohol | 15.0 |
| Hyaluronic acid extract | 5.0 |
| Beta glucan | 7.0 |
| Allantoin | 0.1 |
| Nonyl phenyl ether | 0.4 |
| Polysorbate 60 | 1.2 |
| Ethanol preservative | 6.0 |
| Antiseptic, Colorant, Fragrance | Adequate |
| Purified water | Balance |

[Formulation Example 15] Soft Capsule 9 mg of vitamin E, 9 mg of vitamin C, 2 mg of palm oil, 8 mg of hydrogenated vegetable oil, 4 mg of yellow wax and 9 mg of lecithin were mixed to the nanoemulsion composition of Example 51, and mixed according to a commonly used method to prepare a soft capsule filling solution. Soft capsules were prepared by filling 400 mg of the solution per capsule. In addition, a soft capsule sheet was prepared in a ratio of 66 parts by weight of gelatin, 24 parts by weight of glycerin, and 10 parts by weight of sorbitol solution, separately from the above, and the filling solution was filled to prepare a soft capsule containing 400 mg of the composition.

[Formulation Example 16] Tablet 9 mg of vitamin E, 9 mg of vitamin C, 200 mg of galactooligosaccharide, 60 mg of lactose, and 140 mg of maltose were mixed to the nanoemulsion composition of Example 51, granulated using a fluidized bed dryer, and 6 mg of sugar ester was added thereto. 500 mg of these compositions were compressed in a commonly used method to prepare tablets.

[Formulation Example 17] Injection

Injection was prepared in a commonly used method according to the composition shown in Table 25 below.

TABLE 25

| Ingredients | Content (mg) |
| --- | --- |
| Nanoemulsion composition of Example 51 | 10.0 |
| Sterile distilled water for injection | Adequate |
| pH controller | Adequate |

[Formulation Example 18] Health Drink

A health drink was prepared in a commonly used method according to the composition shown in Table 26 below.

TABLE 26

| Ingredients | Content(mg) |
| --- | --- |
| Nanoemulsion composition of Example 51 | 100 |
| Citric acid/oligosaccharide/taurine | Adequate |

The present disclosure relates to various aspects, and includes at least the following aspects.

[Aspect 1] A nanoemulsion composition of oxygen gas sustained release, including a water phase part containing water; and an oil phase part dispersed in the water phase part and made of nanoparticle containing a perfluorocarbon compound, wherein the oil phase part contains oxygen gas, and the oxygen gas is released in sustained release.

[Aspect 2] In the composition of aspect 1, an average diameter of the nanoparticle is 100 nm to 300 nm.

[Aspect 3] In the composition of aspect 1 or 2, the oxygen gas is collected in an amount of 1 ppm (v/w) to 35 ppm (v/w) based on a total weight of the nanoemulsion composition.

[Aspect 4] In the composition of any one of aspects 1 to 3, the perfluorocarbon compound is a perfluoroalkyl halide.

[Aspect 5] In the composition of any one of aspects 1 to 4, the perfluorocarbon compound is a perfluorooctylbromide (PFOB).

[Aspect 6] In the composition of any one of aspects 1 to 5, the perfluorocarbon compound is one or more of a chain perfluorinated aliphatic hydrocarbon of 1 to 12 carbon atoms and a cyclic perfluorinated aliphatic hydrocarbon of 3 to 12 carbon atoms having 1 or 2 rings.

[Aspect 7] In the composition of any one of aspects 1 to 6, the perfluorocarbon compound is a combination of the chain perfluorinated aliphatic hydrocarbon of 1 to 12 carbon atoms and the cyclic perfluorinated aliphatic hydrocarbon of 3 to 12 carbon atoms having 1 or 2 rings.

[Aspect 8] In the composition of any one of aspects 1 to 7, the perfluorocarbon compound is one or more of perfluorodecalin (PFD) and perfluorohexane (PFH).

[Aspect 9] In the composition of any one of aspects 1 to 8, the perfluorocarbon compound is a combination of perfluorodecalin (PFD) and perfluorohexane (PFH), and a content ratio of the perfluorodecalin (PFD) and the perfluorohexane (PFH) is 6:1 to 1:3 by weight.

[Aspect 10] In the composition of any one of aspects 1 to 9, a content of the perfluorocarbon compound is 5 to 80% by weight based on a total weight of the nanoemulsion composition.

[Aspect 11] In the composition of any one of aspects 1 to 10, the nanoemulsion composition further comprises one or more of phospholipid, polyglycerin stearic acid ester and fatty acid ester of sorbitan as a main surfactant, the nanoemulsion composition further comprises one or more of cholesterol, glyceryl diester, inulin fatty acid ester, polyglycerin lauric acid ester, carboxylate salt of glutamic acid, and fatty acid ester of ethoxylated sorbitan as auxiliary surfactant.

[Aspect 12] In the composition of any one of aspects 1 to 11, a total content of the main surfactant and the auxiliary surfactant is 0.1 to 10% by weight based on a total weight of the nanoemulsion composition.

[Aspect 13] In the composition of any one of aspects 1 to 12, a content ratio of the main surfactant and the auxiliary surfactant is 10:1 to 1:3 by weight.

[Aspect 14] In the composition of any one of aspects 1 to 13, the phospholipid is one or more selected from the group consisting of hydrogenated lecithin and phosphatidylcholine, the polyglycerol stearic acid ester is polyglyceryl-10 stearate, and the fatty acid ester of sorbitan is sorbitan monooleate (Span 80).

[Aspect 15] In the composition of any one of aspects 1 to 14, the glyceryl diester is glyceryl stearate citrate, the inulin fatty acid ester is inulin lauryl carbamate, the polyglycerin lauric acid ester is polyglyceryl-10 laurate, the carboxylate salt of glutamic acid is sodium stearoyl glutamate, and the fatty acid ester of the ethoxylated sorbitan is PEG-20 sorbitan monooleate (Tween 80).

[Aspect 16] In the composition of any one of aspects 1 to 15, a concentration of the oxygen gas reaches equilibrium at 10 seconds or more after the composition starts dissolution.

[Aspect 17] In the composition of any one of aspects 1 to 16, the composition prevents hair loss or promotes hair growth.

[Aspect 18] In the composition of any one of aspects 1 to 17, an additional active ingredient for hair loss prevention or hair growth promotion is further included.

[Aspect 19] In the composition of any one of aspects 1 to 18, the composition has a formulation for external application to skin.

[Aspect 20] In the composition of any one of aspects 1 to 19, the composition is a cosmetic composition, a pharmaceutical composition or a food composition.

[Aspect 21] A method for preparing the composition according to any one of aspects 1 to 19, comprising the steps of preparing a first mixture by mixing water, oil;

one or more of the phospholipid, the polyglycerin stearic acid ester and the fatty acid ester of sorbitan as the main surfactant; and one or more of the cholesterol, the glyceryl diester, the inulin fatty acid ester, the polyglycerin lauric acid ester, the carboxylate salt of glutamic acid, and the fatty acid ester of ethoxylated sorbitan as the auxiliary surfactant; preparing a second mixture by adding the perfluorocarbon compound to the first mixture; preparing a crude emulsion by homogenizing the second mixture; and bubbling the oxygen into the crude emulsion.

Although the present invention has been described with reference to the above-mentioned preferred embodiments, various modifications and variations are possible without departing from the spirit and scope of the invention. Accordingly, it is intended that the appended claims cover such modifications and variations as fall within the scope of the present invention.

What is claimed is:

1. A nanoemulsion composition of oxygen gas sustained release, comprising:
    a water phase part containing water; an oil phase part dispersed in the water phase part and made of nanoparticle containing a perfluorocarbon compound;
    a main surfactant comprising a fatty acid ester of sorbitan; and
    an auxiliary surfactant comprising a fatty acid ester of ethoxylated sorbitan,
    wherein the oil phase part contains oxygen gas, and the oxygen gas is released in sustained release,
    wherein an average diameter of the nanoparticle is 100 nm to 250 nm, and
    wherein a content ratio of the main surfactant and the auxiliary surfactant is 3:1 to 1:1 by weight.

2. The composition according to claim 1, wherein the oxygen gas is collected in an amount of 1 ppm (v/w) to 35 ppm (v/w) based on a total weight of the nanoemulsion composition.

3. The composition according to claim 1, wherein the perfluorocarbon compound is a perfluoroalkyl halide or a perfluorooctylbromide (PFOB).

4. The composition according to claim 1, wherein the perfluorocarbon compound is one or more of selected from the group consisting of a chain perfluorinated aliphatic hydrocarbon of 1 to 12 carbon atoms and a cyclic perfluorinated aliphatic hydrocarbon of 3 to 12 carbon atoms having 1 or 2 rings.

5. The composition according to claim 4, wherein the perfluorocarbon compound is a combination of the chain perfluorinated aliphatic hydrocarbon of 1 to 12 carbon atoms and the cyclic perfluorinated aliphatic hydrocarbon of 3 to 12 carbon atoms having 1 or 2 rings.

6. The composition according to claim 4, wherein the perfluorocarbon compound is perfluorodecalin (PFD), and perfluorohexane (PFH), or a combination thereof.

7. The composition according to claim 5, wherein the perfluorocarbon compound is a combination of perfluorodecalin (PFD) and perfluorohexane (PFH), and a content ratio of the perfluorodecalin (PFD) and the perfluorohexane (PFH) is 6:1 to 1:3 by weight.

8. The composition according to claim 1, wherein a content of the perfluorocarbon compound is 5 to 80% by weight based on a total weight of the nanoemulsion composition.

9. The composition according to claim 1, wherein a total content of the main surfactant and the auxiliary surfactant is 0.1 to 10% by weight based on a total weight of the nanoemulsion composition.

10. The composition according to claim 1, wherein the fatty acid ester of sorbitan is sorbitan monooleate.

11. The composition according to claim 1, wherein the fatty acid ester of the ethoxylated sorbitan is PEG-20 sorbitan monooleate.

12. The composition according to claim 1, wherein a concentration of the oxygen gas reaches equilibrium at 10 seconds or more after the composition starts dissolution.

13. The composition according to claim 1, wherein the composition has a formulation for external application to skin.

14. The composition according to claim 1, wherein the composition is a cosmetic composition, a pharmaceutical composition or a food composition.

15. A method for preventing hair loss or promoting hair growth of a subject in need thereof, comprising administering an effective amount of the composition according to claim 1 to the subject.

16. The method according to claim 15, the composition further comprises an additional active ingredient for hair loss prevention or hair growth promotion.

17. A method for preparing the composition according to claim 1, comprising:
    preparing a first mixture by mixing water; oil; the fatty acid ester of sorbitan as the main surfactant; and the fatty acid ester of ethoxylated sorbitan as the auxiliary surfactant;
    preparing a second mixture by adding the perfluorocarbon compound to the first mixture;
    preparing a crude emulsion by homogenizing the second mixture; and
    bubbling oxygen into the crude emulsion to give the nanoemulsion composition of oxygen gas-sustained release.

* * * * *